US010350365B2

(12) United States Patent
Gross et al.

(10) Patent No.: US 10,350,365 B2
(45) Date of Patent: Jul. 16, 2019

(54) EXTERNAL DRUG PUMP

(71) Applicant: MEDIMOP Medical Projects Ltd., Ra'anana (IL)

(72) Inventors: Yossi Gross, Moshav Mazor (IL); Oz Cabiri, Macabim-Reut (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 0 days.

(21) Appl. No.: 15/655,068

(22) Filed: Jul. 20, 2017

(65) Prior Publication Data
US 2017/0312450 A1     Nov. 2, 2017

Related U.S. Application Data

(60) Division of application No. 14/593,051, filed on Jan. 9, 2015, now Pat. No. 9,782,545, which is a
(Continued)

(51) Int. Cl.
*A61M 5/14*     (2006.01)
*A61M 5/31*     (2006.01)
(Continued)

(52) U.S. Cl.
CPC ...... *A61M 5/31596* (2013.01); *A61M 5/1452* (2013.01); *A61M 5/1456* (2013.01);
(Continued)

(58) Field of Classification Search
CPC .............. A61M 5/145; A61M 5/14248; A61M 2005/2414; A61M 5/24
See application file for complete search history.

(56) References Cited

U.S. PATENT DOCUMENTS 232,432 A      9/1880  Allison
1,795,630 A    3/1931  Wilson
(Continued)

FOREIGN PATENT DOCUMENTS

CN     1505535 A      6/2004
CN    101227943 A     7/2008
(Continued)

OTHER PUBLICATIONS

Office Action dated May 18, 2018 in EP 14166591.9.
(Continued)

*Primary Examiner* — Bhisma Mehta
*Assistant Examiner* — Matthew A Engel
(74) *Attorney, Agent, or Firm* — Panitch Schwarze Belisario & Nadel LLP

(57) ABSTRACT

Apparatus is described for administering a substance to a subject. A vial contains the substance and a stopper is disposed within the vial and is slidably coupled to the vial. A first threaded element is (a) rotatable with respect to the vial and (b) substantially immobile proximally with respect to the vial during rotation of the first threaded element. A second threaded element is threadedly coupled to the first threaded element. At least a distal end of the second threaded element is substantially non-rotatable with respect to the vial, and the distal end of the second threaded element defines a coupling portion that couples the second threaded element to the stopper. The first threaded element, by rotating, linearly advances the stopper and at least the distal end of the second threaded element toward a distal end of the vial. Other embodiments are also described.

12 Claims, 12 Drawing Sheets

Related U.S. Application Data continuation of application No. 12/244,666, filed on Oct. 2, 2008, now Pat. No. 9,173,997.

(60) Provisional application No. 60/997,459, filed on Oct. 2, 2007.

(51) Int. Cl.

| | | |
|---|---|---|
| *A61M 5/142* | (2006.01) | |
| *A61M 5/145* | (2006.01) | |
| *A61M 5/158* | (2006.01) | |
| *A61M 5/168* | (2006.01) | |
| *A61M 5/172* | (2006.01) | |
| *A61M 5/315* | (2006.01) | |
| *F16H 25/12* | (2006.01) | |

(52) U.S. Cl.
CPC .... *A61M 5/14248* (2013.01); *A61M 5/14566* (2013.01); *A61M 5/158* (2013.01); *A61M 5/172* (2013.01); *F16H 25/12* (2013.01); *A61M 5/1413* (2013.01); *A61M 5/16827* (2013.01); *A61M 5/1723* (2013.01); *A61M 5/3146* (2013.01); *A61M 2005/1426* (2013.01); *A61M 2005/14252* (2013.01); *A61M 2005/14268* (2013.01); *A61M 2005/14533* (2013.01); *A61M 2005/31518* (2013.01); *A61M 2205/3523* (2013.01); *A61M 2205/3569* (2013.01); *Y10T 74/18576* (2015.01)

(56) References Cited

U.S. PATENT DOCUMENTS

| | | |
|---|---|---|
| 2,677,373 A | 5/1954 | Barradas |
| 2,702,547 A | 2/1955 | Glass |
| 2,860,635 A | 11/1958 | Wilburn |
| 3,203,269 A | 8/1965 | Perrine |
| 3,212,685 A | 10/1965 | Swan et al. |
| 3,623,474 A | 11/1971 | Heilman et al. |
| 4,195,636 A | 4/1980 | Behnke |
| 4,254,768 A | 3/1981 | Ty |
| 4,273,122 A | 6/1981 | Whitney et al. |
| 4,300,554 A | 11/1981 | Hessberg et al. |
| 4,403,987 A | 9/1983 | Gottinger |
| 4,435,173 A | 3/1984 | Siposs et al. |
| 4,465,478 A | 8/1984 | Sabelman et al. |
| 4,502,488 A | 3/1985 | Degironimo et al. |
| 4,504,263 A | 3/1985 | Steuer et al. |
| 4,564,054 A | 1/1986 | Gustavsson |
| 4,585,439 A | 4/1986 | Michel |
| 4,599,082 A | 7/1986 | Grimard |
| 4,664,654 A | 5/1987 | Strauss |
| 4,685,903 A | 8/1987 | Cable et al. |
| 4,698,055 A | 10/1987 | Sealfon |
| 4,735,311 A | 4/1988 | Lowe et al. |
| 4,810,215 A | 3/1989 | Kaneko |
| 4,867,743 A | 9/1989 | Vaillancourt |
| 4,882,575 A | 11/1989 | Kawahara |
| 4,892,521 A | 1/1990 | Laico et al. |
| 4,919,596 A | 4/1990 | Slate et al. |
| 4,964,866 A | 10/1990 | Szwarc |
| 5,051,109 A | 9/1991 | Simon |
| 5,112,317 A | 5/1992 | Michel |
| 5,190,521 A | 3/1993 | Hubbard et al. |
| 5,300,045 A | 4/1994 | Plassche, Jr. |
| 5,318,522 A | 6/1994 | D'Antonio |
| 5,478,315 A | 12/1995 | Brothers et al. |
| 5,501,665 A | 3/1996 | Jhuboo et al. |
| 5,562,624 A | 10/1996 | Righi et al. |
| 5,624,400 A | 4/1997 | Firth et al. |
| 5,637,095 A | 6/1997 | Nason et al. |
| 5,643,218 A | 7/1997 | Lynn et al. |
| 5,645,530 A | 7/1997 | Boukhny et al. |
| 5,647,853 A | 7/1997 | Feldmann et al. |
| 5,658,256 A | 8/1997 | Shields |
| 5,662,678 A | 9/1997 | Macklin |
| 5,728,075 A | 3/1998 | Levander |
| 5,766,186 A | 6/1998 | Faraz et al. |
| 5,810,784 A | 9/1998 | Tamaro |
| 5,830,187 A | 11/1998 | Kriesel et al. |
| 5,851,197 A | 12/1998 | Marano et al. |
| 5,858,001 A | 1/1999 | Tsals et al. |
| 5,893,842 A | 4/1999 | Imbert |
| 5,894,015 A | 4/1999 | Rechtin |
| 5,919,167 A | 7/1999 | Mulhauser et al. |
| 5,926,596 A | 7/1999 | Edwards et al. |
| 5,944,699 A | 8/1999 | Barrelle et al. |
| 5,968,011 A | 10/1999 | Larsen et al. |
| 5,989,221 A | 11/1999 | Hjertman |
| 5,993,423 A | 11/1999 | Choi |
| 6,033,245 A | 3/2000 | Yamkovoy |
| 6,045,533 A | 4/2000 | Kriesel et al. |
| 6,186,982 B1 | 2/2001 | Gross et al. |
| 6,200,296 B1 | 3/2001 | Dibiasi et al. |
| 6,248,093 B1 | 6/2001 | Moberg |
| 6,270,481 B1 | 8/2001 | Mason et al. |
| 6,287,283 B1 | 9/2001 | Ljunggreen et al. |
| 6,302,633 B1 | 10/2001 | Poe |
| 6,485,461 B1 | 11/2002 | Mason et al. |
| 6,485,465 B2 | 11/2002 | Moberg et al. |
| 6,511,336 B1 | 1/2003 | Turek et al. |
| 6,554,800 B1 | 4/2003 | Nezhadian et al. |
| 6,565,541 B2 | 5/2003 | Sharp |
| 6,595,956 B1 | 7/2003 | Gross et al. |
| 6,656,159 B2 | 12/2003 | Flaherty |
| 6,659,980 B2 | 12/2003 | Moberg et al. |
| 6,699,218 B2 | 3/2004 | Flaherty et al. |
| 6,722,916 B2 | 4/2004 | Buccinna et al. |
| 6,743,211 B1 | 6/2004 | Prausnitz et al. |
| 6,749,587 B2 | 6/2004 | Flaherty |
| 6,800,071 B1 | 10/2004 | McConnell et al. |
| 6,905,298 B1 | 6/2005 | Haring |
| 6,960,192 B1 | 11/2005 | Flaherty et al. |
| 6,997,727 B1 | 2/2006 | Legrady et al. |
| 7,033,338 B2 | 4/2006 | Vilks et al. |
| 7,034,223 B2 | 4/2006 | Fan et al. |
| 7,060,054 B2 | 6/2006 | Nissels |
| 7,225,694 B2 | 6/2007 | Said |
| 7,250,037 B2 | 7/2007 | Shermer et al. |
| 7,291,132 B2 | 11/2007 | DeRuntz et al. |
| 7,291,159 B2 | 11/2007 | Schmelzeisen-Redeker et al. |
| 7,407,493 B2 | 8/2008 | Cane' |
| 7,442,186 B2 | 10/2008 | Blomquist |
| 7,488,181 B2 | 2/2009 | van Haaster |
| 7,501,587 B2 | 3/2009 | English |
| 7,503,786 B2 | 3/2009 | Kato et al. |
| 7,540,858 B2 | 6/2009 | DiBiasi |
| 7,704,088 B2 | 4/2010 | Sakamoto |
| 7,717,903 B2 | 5/2010 | Estes et al. |
| 7,736,344 B2 | 6/2010 | Moberg et al. |
| 7,766,867 B2 | 8/2010 | Lynch et al. |
| 7,794,426 B2 | 9/2010 | Briones et al. |
| 7,938,803 B2 | 5/2011 | Mernoe et al. |
| 7,967,795 B1 | 6/2011 | Cabiri |
| 8,057,436 B2 | 11/2011 | Causey et al. |
| 8,062,253 B2 | 11/2011 | Nielsen et al. |
| 8,105,293 B2 | 1/2012 | Pickhard |
| 8,152,779 B2 | 4/2012 | Cabiri |
| 8,157,769 B2 | 4/2012 | Cabiri |
| 8,172,591 B2 | 5/2012 | Wertz |
| 8,177,749 B2 | 5/2012 | Slate et al. |
| 8,221,356 B2 | 7/2012 | Enggaard et al. |
| 8,348,898 B2 | 1/2013 | Cabiri |
| 8,425,468 B2 | 4/2013 | Weston |
| 8,512,295 B2 | 8/2013 | Evans et al. |
| 8,523,803 B1 | 9/2013 | Favreau |
| 8,551,046 B2 | 10/2013 | Causey et al. |
| 8,562,364 B2 | 10/2013 | Lin et al. |
| 8,603,026 B2 | 12/2013 | Favreau |
| 8,603,027 B2 | 12/2013 | Favreau |
| 8,622,966 B2 | 1/2014 | Causey et al. |
| 8,915,882 B2 | 12/2014 | Cabiri |
| 8,979,802 B2 | 3/2015 | Woehr |

(56) References Cited

U.S. PATENT DOCUMENTS

| | | | |
|---|---|---|---|
| 9,011,164 B2 | 4/2015 | Filman et al. | |
| 9,072,827 B2 | 7/2015 | Cabiri | |
| 9,149,575 B2 | 10/2015 | Cabiri | |
| 9,173,997 B2 | 11/2015 | Gross et al. | |
| D747,799 S | 1/2016 | Norton et al. | |
| 9,259,532 B2 | 2/2016 | Cabiri | |
| 9,314,569 B2 | 4/2016 | Causey et al. | |
| 9,345,836 B2 | 5/2016 | Cabiri et al. | |
| 9,350,634 B2 | 5/2016 | Fadell | |
| 9,393,365 B2 | 7/2016 | Cabiri | |
| 9,421,323 B2 | 8/2016 | Cabiri et al. | |
| 9,452,261 B2 | 9/2016 | Alon | |
| 9,522,234 B2 | 12/2016 | Cabiri | |
| 9,539,388 B2 | 1/2017 | Causey et al. | |
| 9,572,926 B2 | 2/2017 | Cabiri | |
| 9,656,019 B2 | 5/2017 | Cabiri et al. | |
| 9,782,545 B2 * | 10/2017 | Gross | A61M 5/14566 |
| 2001/0018937 A1 | 9/2001 | Nemoto | |
| 2001/0025168 A1 | 9/2001 | Gross et al. | |
| 2001/0034502 A1 | 10/2001 | Moberg et al. | |
| 2001/0041869 A1 | 11/2001 | Causey et al. | |
| 2002/0016569 A1 | 2/2002 | Critchlow et al. | |
| 2002/0029018 A1 | 3/2002 | Jeffrey | |
| 2002/0151855 A1 | 10/2002 | Douglas et al. | |
| 2002/0169215 A1 | 11/2002 | Meng | |
| 2003/0009133 A1 * | 1/2003 | Ramey | A61M 5/1456 604/155 |
| 2003/0014018 A1 | 1/2003 | Giambattista et al. | |
| 2003/0216683 A1 | 11/2003 | Shekalim | |
| 2004/0000818 A1 | 1/2004 | Preuthun et al. | |
| 2004/0049160 A1 | 3/2004 | Hsieh et al. | |
| 2004/0082911 A1 | 4/2004 | Tiu et al. | |
| 2004/0092873 A1 | 5/2004 | Moberg | |
| 2004/0127857 A1 | 7/2004 | Shemesh et al. | |
| 2004/0210196 A1 | 10/2004 | Bush, Jr. et al. | |
| 2005/0033234 A1 | 2/2005 | Sadowski et al. | |
| 2005/0038391 A1 | 2/2005 | Wittland et al. | |
| 2005/0171512 A1 | 8/2005 | Flaherty | |
| 2005/0203461 A1 | 9/2005 | Flaherty et al. | |
| 2005/0283114 A1 | 12/2005 | Bresina et al. | |
| 2006/0124269 A1 | 6/2006 | Miyazaki et al. | |
| 2006/0206054 A1 | 9/2006 | Shekalim | |
| 2006/0264888 A1 | 11/2006 | Moberg et al. | |
| 2006/0264890 A1 | 11/2006 | Moberg et al. | |
| 2006/0293722 A1 | 12/2006 | Slatkine et al. | |
| 2007/0025879 A1 | 2/2007 | Vandergaw | |
| 2007/0073228 A1 | 3/2007 | Mernoe et al. | |
| 2007/0118405 A1 | 5/2007 | Campbell et al. | |
| 2007/0167912 A1 | 7/2007 | Causey et al. | |
| 2007/0179444 A1 | 8/2007 | Causey et al. | |
| 2007/0185449 A1 | 8/2007 | Mernoe | |
| 2007/0197954 A1 | 8/2007 | Keenan | |
| 2007/0203454 A1 | 8/2007 | Shermer et al. | |
| 2008/0033367 A1 | 2/2008 | Haury et al. | |
| 2008/0033393 A1 | 2/2008 | Edwards et al. | |
| 2008/0097381 A1 | 4/2008 | Moberg et al. | |
| 2008/0215013 A1 | 9/2008 | Felix-Faure | |
| 2008/0319383 A1 | 12/2008 | Byland et al. | |
| 2009/0012478 A1 | 1/2009 | Weston | |
| 2009/0076383 A1 | 3/2009 | Toews et al. | |
| 2009/0088694 A1 | 4/2009 | Carter et al. | |
| 2009/0093763 A1 | 4/2009 | Gonnelli et al. | |
| 2009/0093792 A1 | 4/2009 | Gross et al. | |
| 2009/0093793 A1 | 4/2009 | Gross et al. | |
| 2009/0143730 A1 | 6/2009 | De Polo et al. | |
| 2009/0204076 A1 | 8/2009 | Liversidge | |
| 2009/0299288 A1 | 12/2009 | Sie et al. | |
| 2009/0299290 A1 | 12/2009 | Moberg | |
| 2009/0326459 A1 | 12/2009 | Shipway et al. | |
| 2010/0076382 A1 | 3/2010 | Weston | |
| 2010/0168683 A1 | 7/2010 | Cabiri | |
| 2011/0066131 A1 | 3/2011 | Cabiri | |
| 2011/0092915 A1 | 4/2011 | Olson et al. | |
| 2011/0112504 A1 | 5/2011 | Causey et al. | |
| 2011/0224616 A1 | 9/2011 | Slate et al. | |
| 2012/0022496 A1 | 1/2012 | Causey et al. | |
| 2012/0041387 A1 | 2/2012 | Bruggemann et al. | |
| 2012/0172817 A1 | 7/2012 | Bruggemann et al. | |
| 2013/0085457 A1 | 4/2013 | Schiff et al. | |
| 2013/0110049 A1 | 5/2013 | Cronenberg et al. | |
| 2013/0190693 A1 | 7/2013 | Ekman et al. | |
| 2013/0245596 A1 | 9/2013 | Cabiri et al. | |
| 2013/0267895 A1 | 10/2013 | Hemmingsen | |
| 2013/0296799 A1 | 11/2013 | Degtiar et al. | |
| 2013/0304021 A1 | 11/2013 | Cabiri et al. | |
| 2013/0310753 A1 | 11/2013 | Cabiri | |
| 2013/0331791 A1 | 12/2013 | Gross et al. | |
| 2014/0018735 A1 | 1/2014 | Causey et al. | |
| 2014/0121633 A1 | 5/2014 | Causey et al. | |
| 2014/0148784 A1 | 5/2014 | Anderson et al. | |
| 2014/0174223 A1 | 6/2014 | Gross et al. | |
| 2014/0194854 A1 | 7/2014 | Tsals | |
| 2014/0236087 A1 | 8/2014 | Alderete, Jr. et al. | |
| 2015/0119798 A1 * | 4/2015 | Gross | A61M 5/14566 604/67 |
| 2015/0374926 A1 | 12/2015 | Gross et al. | |
| 2016/0030665 A1 | 2/2016 | Cabiri | |
| 2016/0296716 A1 | 10/2016 | Cabiri et al. | |
| 2016/0346478 A1 | 12/2016 | Bar-El et al. | |

FOREIGN PATENT DOCUMENTS

| | | |
|---|---|---|
| CN | 101448536 A | 6/2009 |
| CN | 101522235 A | 9/2009 |
| CN | 101541362 A | 9/2009 |
| CN | 201692438 U | 1/2011 |
| CN | 102378638 A | 3/2012 |
| DE | 1064693 B | 9/1959 |
| DE | 19717107 A1 | 11/1998 |
| EP | 1003581 B1 | 11/2000 |
| EP | 1219312 A2 | 7/2002 |
| EP | 1530979 A1 | 5/2005 |
| FR | 2770136 A1 | 4/1999 |
| JP | H09-505758 A | 6/1997 |
| JP | 2002528676 A | 9/2002 |
| JP | 2009502273 A | 1/2009 |
| WO | 9307922 A1 | 4/1993 |
| WO | 9407553 A1 | 4/1994 |
| WO | 9700091 A1 | 1/1997 |
| WO | 200130421 A2 | 5/2001 |
| WO | 200172357 A2 | 10/2001 |
| WO | 0187384 A1 | 11/2001 |
| WO | 200238204 A2 | 5/2002 |
| WO | 02072182 A1 | 9/2002 |
| WO | 04000397 A1 | 12/2003 |
| WO | 2004105841 A1 | 12/2004 |
| WO | 2005072795 A2 | 8/2005 |
| WO | 2006037434 A1 | 4/2006 |
| WO | 06069380 A1 | 6/2006 |
| WO | 2006121921 A2 | 11/2006 |
| WO | 2007017052 A1 | 2/2007 |
| WO | 2007051563 A1 | 5/2007 |
| WO | 20070073228 A1 | 6/2007 |
| WO | 2009044401 | 4/2009 |
| WO | 2009144085 A2 | 12/2009 |
| WO | 2010089313 A1 | 8/2010 |
| WO | 2011090956 A2 | 7/2011 |
| WO | 2015114158 A1 | 8/2015 |

OTHER PUBLICATIONS

West Introduces The Daikyo Crystal Zenith RU Prefillable Syringe, Pharmaceutical Online, Jun. 2008, downloaded from webpage: http://www.pharmaceuticalonline.com/article.mvc/west-introduces-prefillable-syringe-system, Download date: Jan. 2009, original posting date: Jun. 2008, 2 pages.

Copaxone®, Innovative Drugs, Teva Pharmaceuticals, downloaded from webpage: http://tevapharm.com/copaxone/, Download date: Jan. 2009, original posting date: unknown, 3 pages.

Office Action dated Apr. 5, 2010 in U.S. Appl. No. 12/244,666 by Gross.

(56) References Cited

OTHER PUBLICATIONS

Office Action dated Jul. 7, 2014 in U.S. Appl. No. 12/244,666 by Gross.
Office Action dated Mar. 10, 2015 in U.S. Appl. No. 12/244,666 by Gross.
Office Action dated Sep. 18, 2015 in U.S. Appl. No. 13/874,085 by Cabiri.
Office Action dated May 25, 2016 in U.S. Appl. No. 14/874,017 by Cabiri.
Office Action dated Jun. 10, 2016 in U.S. Appl. No. 13/964,651 by Gross.
Int'l Search Report and Written Opinion dated May 13, 2009 in Int'l Application No. PCT/IL2008/001312.
Int'l Preliminary Report on Patentability dated Apr. 7, 2010 in Int'l Application No. PCT/IL2008/001312.
Office Action dated May 3, 2012 in CN Application No. 200880117084.X.
Office Action dated Jan. 30, 2013 in CN Application No. 200880117084.X.
Office Action dated Aug. 15, 2013 in CN Application No. 200880117084.X.
Office Action dated Mar. 5, 2014 in CN Application No. 200880117084.X.
Extended Search Report dated Feb. 23, 2015 in EP Application No. 14166596.8.
Search Report dated Nov. 24, 2015 in EP Application No. 14166592.7.
Extended Search Report dated Mar. 8, 2016 in EP Application No. 14166592.7.
Extended Search Report dated Feb. 23, 2015 in EP Application No. 14166591.9.
Office Action dated Jan. 8, 2013 in JP Application No. 2010-527595.
Int'l Search Report dated Oct. 12, 2011 in Int'l Application No. PCT/US2011/021605.
Int'l Written Opinion dated Jul. 19, 2012 in Int'l Application No. PCT/US2011/021605.
Int'l Preliminary Report on Patentability dated Feb. 7, 2013 in Int'l Application No. PCT/US2011/021605.
Office Action dated Nov. 5, 2013 in JP Application No. 2010-527595.
Office Action dated Apr. 5, 2010 in U.S. Appl. No. 12/244,688 by Gross.
Extended Search Report dated Aug. 7, 2014 in EP Application No. 14171477.4.
Office Action dated Nov. 2, 2014 in CN Application No. 201180006571.0.
Office Action dated Jun. 2, 2016 in CN Application No. 2014101783189.
Search Report dated Oct. 14, 2016 in CN Application No. 2014101783742.
Office Action dated Oct. 28, 2016 in CN Application No. 2014101783742.
Office Action dated Nov. 10, 2016 in U.S. Appl. No. 13/874,121, by Degtiar.
Office Action dated Nov. 25, 2016 in U.S. Appl. No. 13/874,017, by Cabiri.
Office Action dated Oct. 5, 2016 in U.S. Appl. No. 13/964,651, by Gross.
Office Action dated Dec. 9, 2016 in U.S. Appl. No. 14/593,051, by Gross.
Office Action dated Jan. 10, 2017 in U.S. Appl. No. 14/193,692, by Gross.
Office Action dated Feb. 16, 2017 in CN Application No. 2014101783189.
Extended European Search Report dated Nov. 10, 2016 in EP Application No. 08808111.2.
Office Action dated Feb. 24, 2017 in U.S. Appl. No. 13/964,651, by Gross.
Extended European Search Report dated Feb. 13, 2017 in EP Application No. 16171626.1.
Office Action dated May 24, 2017 in U.S. Appl. No. 13/874,121, by Degtiar.
Extended European Search Report dated Jul. 3, 2017 in EP Application No. 16190054.3.
Office Action dated May 4, 2017 in CN Application No. 2014101836665.
Office Action dated Jun. 9, 2017 in EP Application No. 14166596.8.
Int'l Search Report and Written Opinion dated Jul. 6, 2017 in Int'l Application No. PCT/US2017/022966.
Office Action dated Jul. 3, 2017 in CN Application No. 2014101783742.
Office Action dated Aug. 14, 2017 in CN Application No. 201410178318.9.
Office Action dated Sep. 28, 2017 in IN Application No. 2528/DELNP/2010.
Office Action dated Nov. 8, 2017 in U.S. Appl. No. 13/874,121, by Degtiar.
Office Action dated Mar. 30, 2018 in U.S. Appl. No. 14/850,450 by Gross.
Office Action dated Mar. 1, 2018 in EP Application No. 14166592.7.
Office Action dated Dec. 4, 2017 in CN Application No. 201410178374.2.
Office Action dated Nov. 13, 2017 in U.S. Appl. No. 14/193,692, by Gross.
Office Action dated Jun. 14, 2018 in U.S. Appl. No. 13/874,121, by Degtiar.
Office Action dated May 14, 2018 in EP Application No. 08808111.2.

* cited by examiner

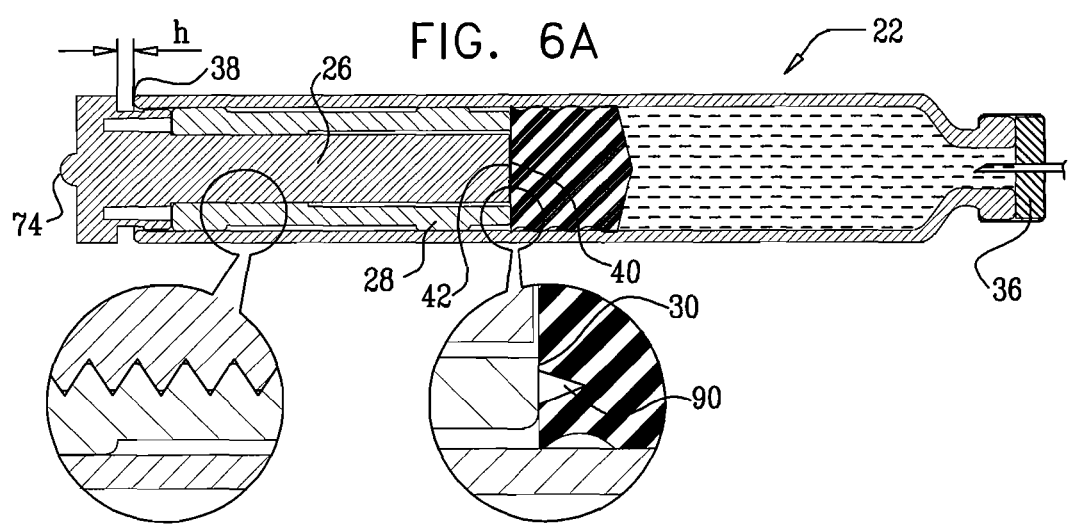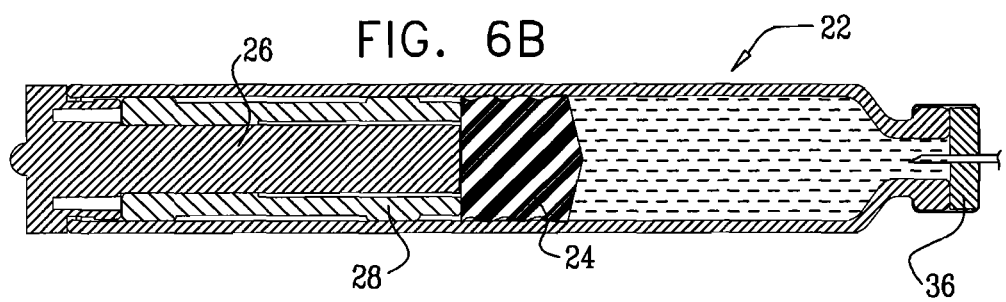

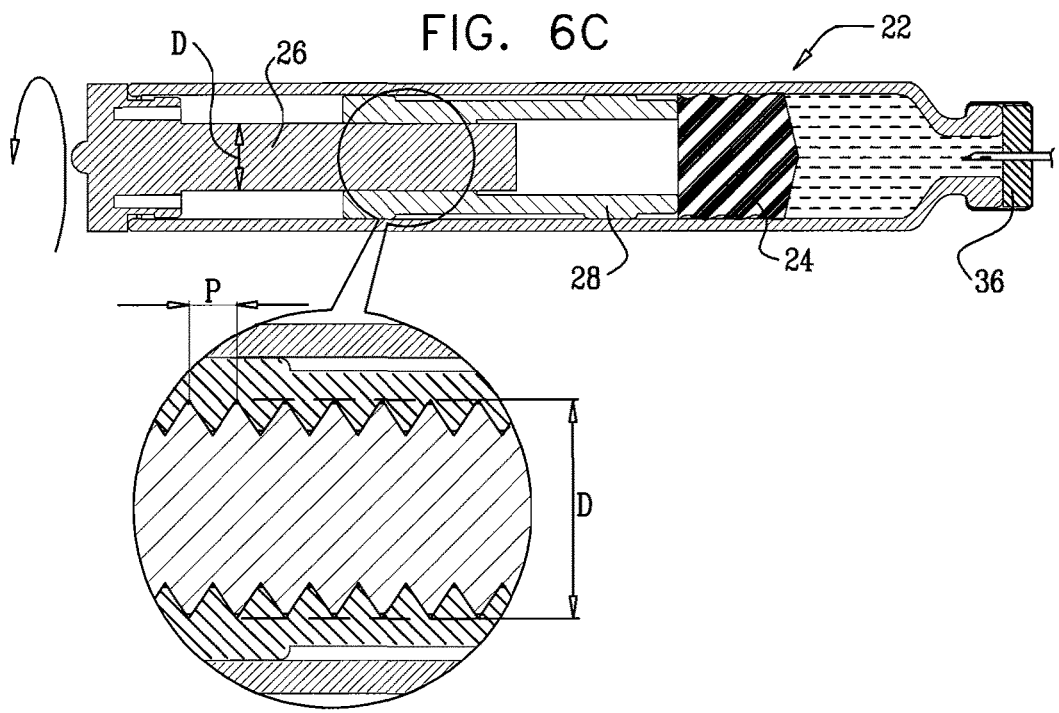
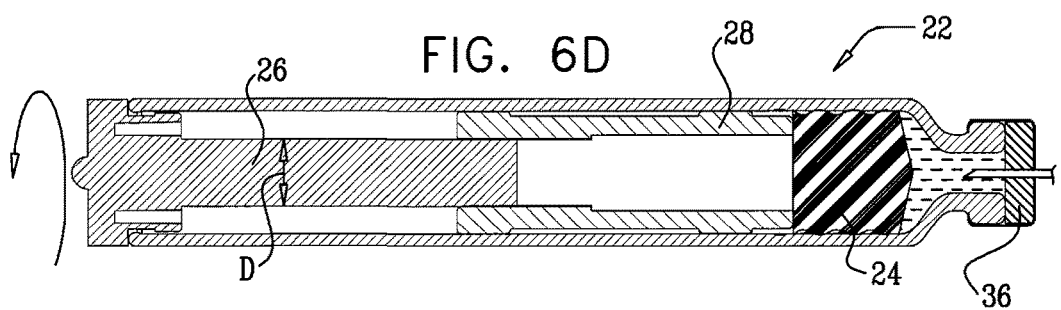
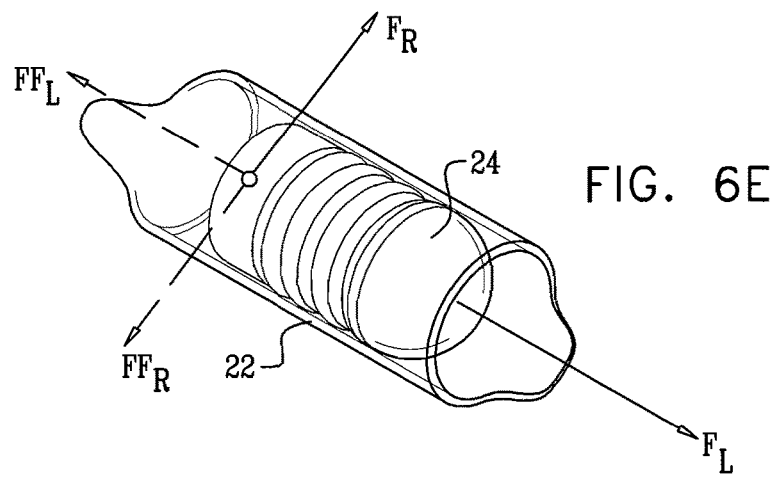

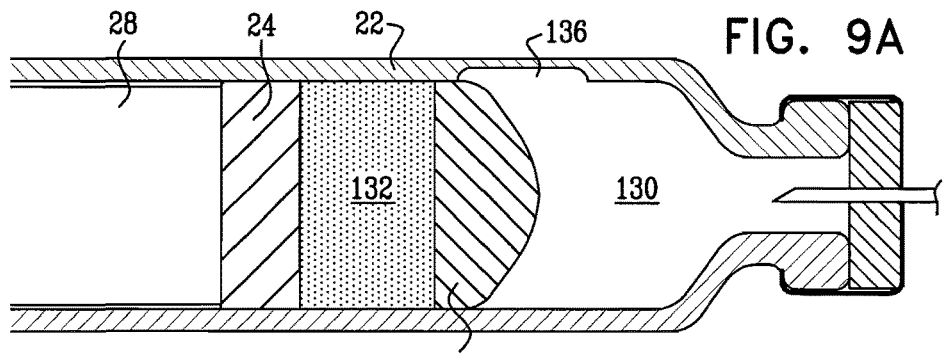
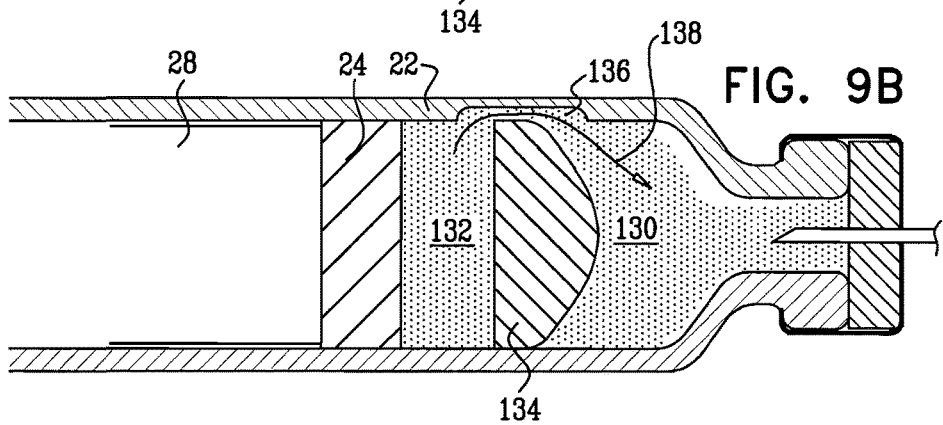
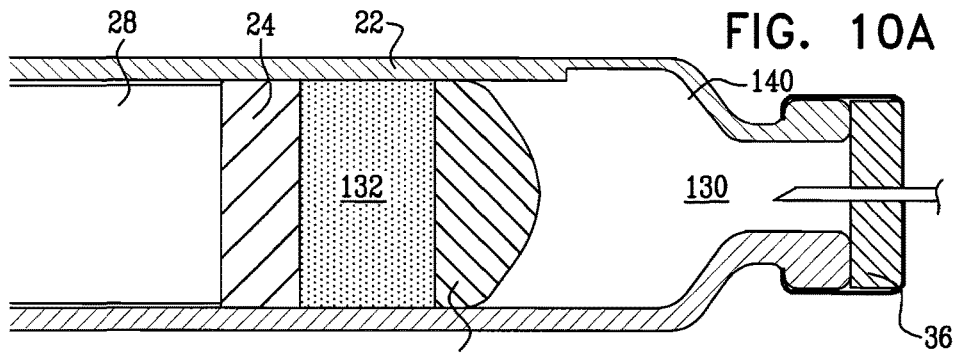
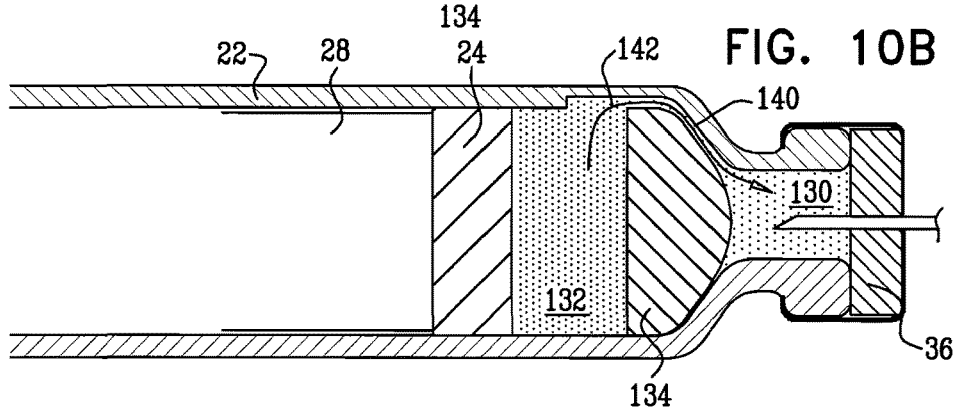

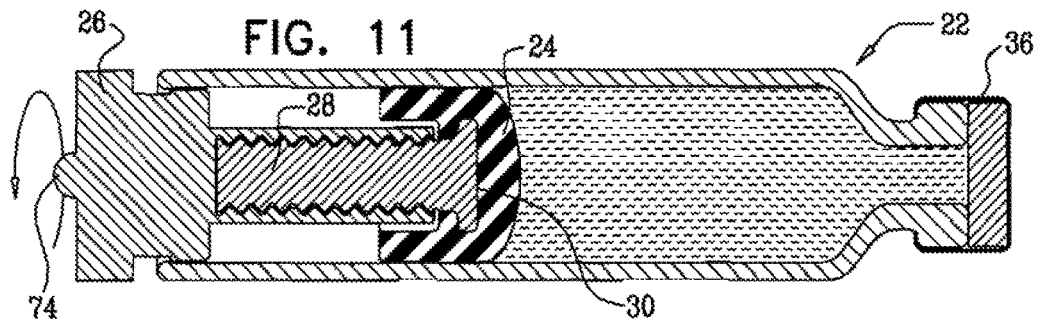
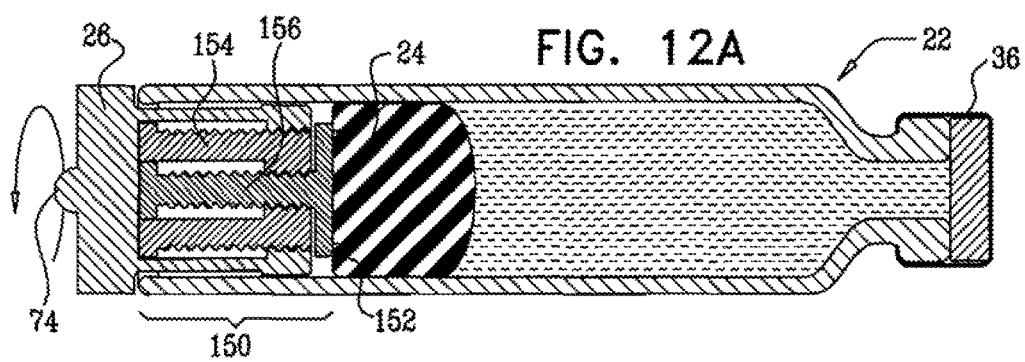
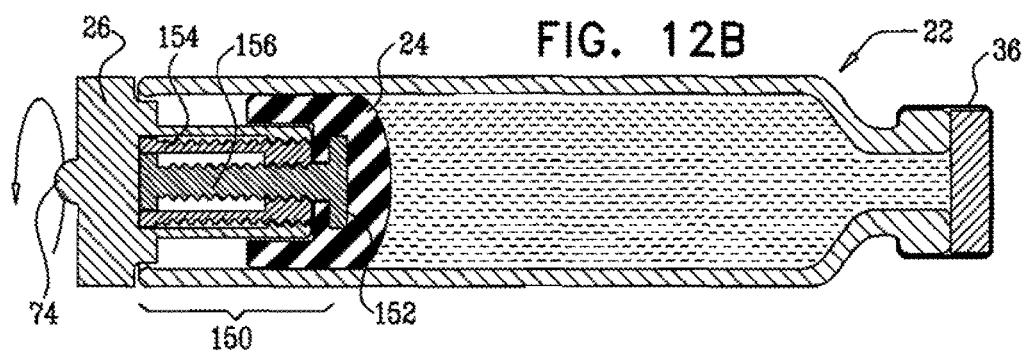
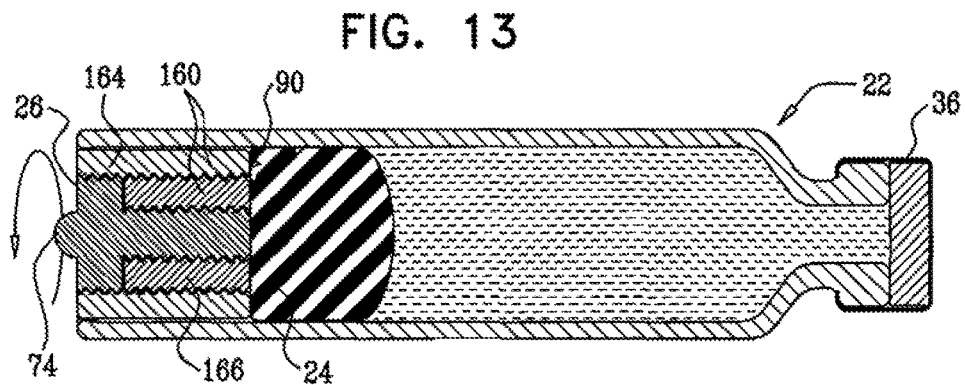

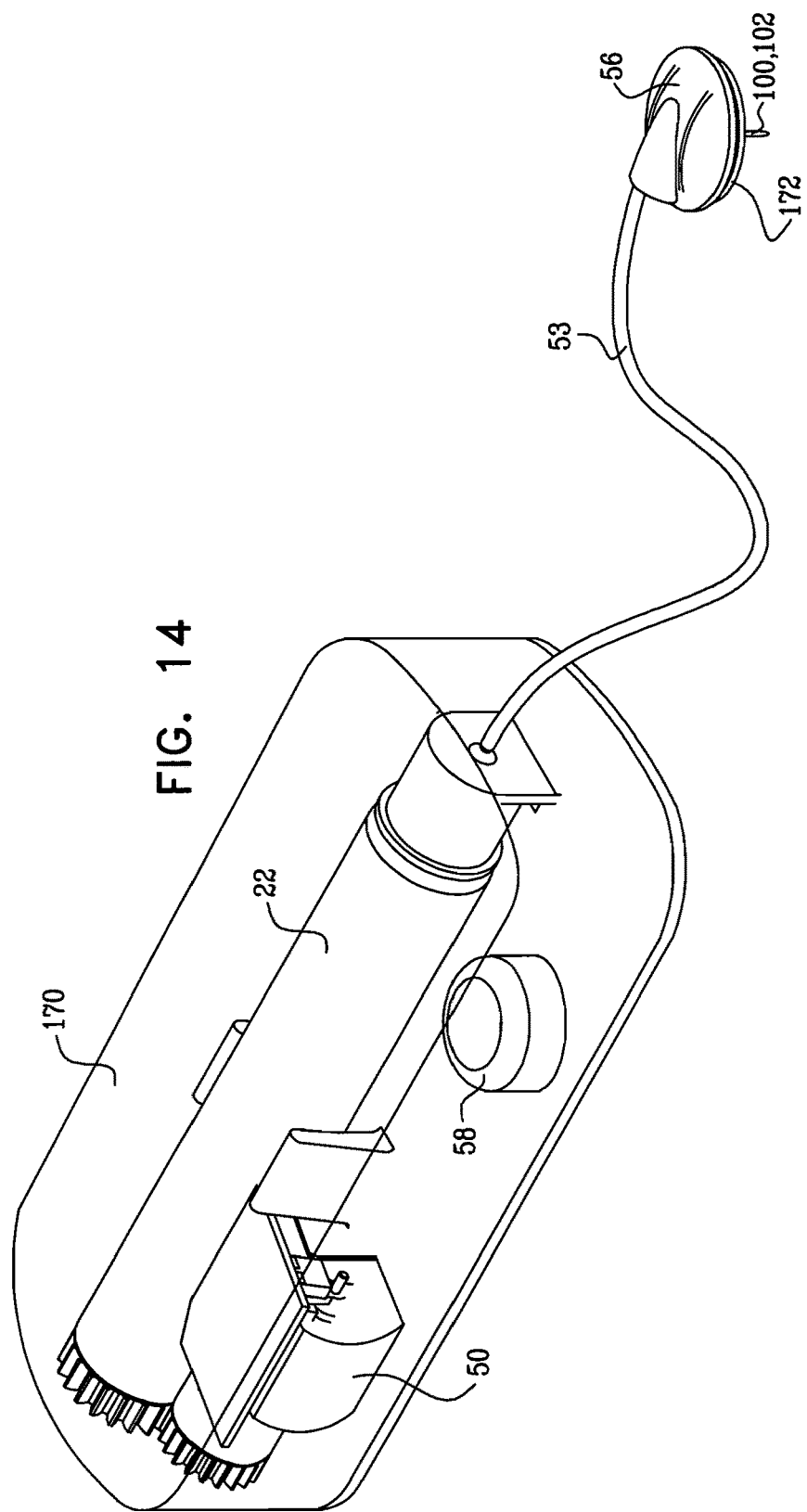

EXTERNAL DRUG PUMP

CROSS-REFERENCE TO RELATED APPLICATIONS

This application is a divisional of U.S. patent application Ser. No. 14/593,051, filed on Jan. 9, 2015, entitled "External Drug Pump," which is a continuation of similarly-titled U.S. patent application Ser. No. 12/244,666, filed on Oct. 2, 2008 and issued on Nov. 3, 2015 as U.S. Pat. No. 9,173,997, which claims the benefit of similarly-titled U.S. Provisional Patent Application No. 60/997,459, filed on Oct. 2, 2007, the contents of each of which are incorporated by reference herein in their entirety.

The present application is related to U.S. patent application Ser. No. 12/244,688, filed on Oct. 2, 2008, entitled "External Drug Pump," the contents of which are incorporated by reference herein. The application is also related to International Patent Application No. PCT/IL2008/001312, filed on Oct. 2, 2008, entitled "External Drug Pump," the contents of which are incorporated by reference herein.

BACKGROUND OF THE INVENTION

The present invention generally relates to external medical apparatus. Specifically, the present invention relates to external drug pumps.

External drug pumps are typically used to deliver to patients substances which contain large molecules which cannot be digested when administered orally. They are commonly used to infuse a basal rate of insulin to subjects suffering from diabetes, as an alternative to insulin injections by an insulin syringe or an insulin pen. Typically, the pump is adhered to the abdomen of the patient and delivers the substance to the patient via a cannula that is inserted into the patient's skin.

U.S. Pat. No. 6,656,159 to Flaherty, describes a device for delivering fluid, such as insulin for example, to a patient. The device includes an exit port assembly, a syringe-like reservoir including a side wall extending towards an outlet connected to the exit port assembly. A threaded lead screw is received in the reservoir and a plunger has an outer periphery linearly slideable along the side wall of the reservoir and an inner periphery threadedly received on the lead screw. The plunger is non-rotatable with respect to the side wall such that rotating the lead screw is described as causing the plunger to advance within the reservoir and force fluid through the outlet. The device also includes a dispenser having a return element for causing rotation of the lead screw, and a shape memory element. A changeable length of the shape memory element decreasing from an uncharged length to a charged length is described as resetting the return element.

U.S. Pat. No. 6,699,218 to Flaherty, describes a device for delivering fluid to a patient, including a passageway having a proximal fluid transport tube, a distal fluid transport tube, and a tubular expansion member coupling the fluid transport tubes. A penetrating member is positioned within the expansion member for axial movement between the fluid transport tubes, and has a sharpened distal tip. The device also includes a dispenser for causing fluid from a reservoir to flow to the proximal fluid transport tube, a housing containing the dispenser and the passageway and including an exit port receiving the distal fluid transport tube, and a connecting member secured to the penetrating member. The connecting member is movable by a user from an exterior of the housing and arranged such that movement causes the penetrating member to move between an extended position for subcutaneously inserting the distal fluid transport tube into a patient, and a retracted position.

U.S. Pat. No. 6,485,461 to Mason, describes a disposable device which is described as accurately and reliably delivering an infusable liquid to a patient. The infusion device includes a housing which defines a bladder chamber. A compressible bladder is disposed in the bladder chamber and is compressed by the housing upon filling the bladder with an infusable liquid to create a pressurized bladder. The infusion devices further includes a delivery system for subcutaneously delivering the infusable liquid to a body. The delivery system includes a collapsible member that supports an injection needle and a cannula. The injection needle is used to insert the cannula into the skin of the body being treated. The cannula is in communication with the bladder during delivery of the infusable liquid. The housing includes microfluidic passageways that allow communication between fluid in the bladder and the cannula.

U.S. Pat. No. 5,851,197 to Marano, describes an injector for automatic placement of a subcutaneous infusion set or the like used for delivering a selected medication to a patient. The injector comprises a spring-loaded plunger having a head for receiving and supporting an infusion set in a position for placement of an insertion needle and related cannula through the skin of a patient at a selected insertion site. The plunger head includes a safety lock mechanism described as engaging and retaining the infusion set during spring-loaded advancement with a controlled force and speed toward the patient's skin to transcutaneously place the insertion needle and cannula. When the plunger head reaches a fully advanced position, with the infusion set placed on the patient, the infusion set is releasable from the safety lock mechanism with minimal force to permit quick and easy separation of the injector.

U.S. Pat. No. 6,960,192 to Flaherty, describes a device for delivering fluid to a person that includes a reservoir for containing a fluid to be delivered to the person; a fluid transport device for dispensing fluid from the reservoir to the person, the fluid transport device including a proximal end in fluid communication with the reservoir and a distal end having a penetrating member for piercing the skin of the person to facilitate the delivery of fluid to the person through the fluid transport device; a housing containing the reservoir and the fluid transport device, the housing including an exit port for receiving the distal end of the fluid transport device upon injection of the distal end into the person and means for securing a first wall of the housing to the skin of the person; and an injection activation device including a driving mechanism contacting the fluid transport device for driving the penetrating member from a first position within the housing, through the exit port to a second position, external to the housing and into the skin of the person.

U.S. Pat. No. 6,905,298 to Haring, describes a nut assembly that will ensure that the shank of a bolt that features a measurable grip length will pass through the contact plane of adjoining members. The nut assembly also allows the desired compressive force in the adjoining members to be attained by using a telescopic feature of the nut to allocate additional thread action for the bolt, enabling the bolt to be drawn into the nut further than what would be allowed by a standard nut. The adaptability of the nut assembly can eliminate the need for washers or shims to adjust the shank penetration of the bolt. The nut assembly is useful for applications in which the specified thread length and the grip length of the bolt is incompatible with the abutment thickness of the adjoining members.

U.S. Pat. No. 1,795,630 to Wilson, describes a screw jack that utilizes a series of telescopic screw threaded sections that may be compactly arranged in the hollow base or housing of the jack when the jack is not in use, or when only a small space is available in which the jack is to be used.

U.S. Pat. No. 5,643,218 to Lynn et al., describes a syringe for the sequential withdrawal of a first liquid and a second liquid. The syringe has a barrel, a proximal piston moveable along the barrel to define a variable volume chamber intermediate the piston and the end of the barrel, and a distal chamber divider piston for separating the variable volume chamber into primary and secondary reservoirs. A flow channel is defined along the syringe for providing flow connection between the primary and secondary reservoirs. An element links the two pistons so that as the proximal piston is moved away from the distal piston, the first liquid enters the first reservoir and thereafter the second liquid enters the secondary reservoir.

Daikyo Crystal Zenith® polymer, manufactured by Daikyo Seiko, Ltd., and used by Daikyo Seiko, Ltd. to manufacture vials, is described as being durable, non-flaking, highly transparent, very low in extractable ions, compatible with a wide pH range, and resistant to high heat.

Copaxone® (glatiramer acetate), manufactured by Teva Pharmaceutical Industries Ltd, is a drug described as helping patients who suffer from relapsing-remitting multiple sclerosis.

The following patent and patent application may be of interest:

U.S. Pat. No. 6,749,587 to Flaherty

U. S. Patent Application Publication 2007/0118405 to Campbell

BRIEF SUMMARY OF THE INVENTION

In some embodiments of the invention, a vial is provided that contains a substance to be administered to a subject. The vial is sealed by a stopper, and has therein first and second threaded elements (e.g., a screw and a nut) that are threadedly coupled to each other. The first threaded element is rotatable with respect to the vial, and is linearly immobile with respect to the vial during rotation of the first threaded element. The first threaded element, by rotating, is configured to linearly advance the stopper and at least the distal end of the second threaded element toward the distal end of the vial, without substantially rotating the second threaded element and the stopper. The distal end of the second threaded element defines a coupling portion that couples the second threaded element to the stopper.

In some embodiments, the stopper impedes rotation of the second threaded element, for example, friction between the stopper and the inside of the vial impedes rotation of the second threaded element. Alternatively or additionally, the vial is shaped such that the vial impedes rotation of the second threaded element.

For some applications, the threaded elements are used in conjunction with a standard, commercially-available vial and/or stopper.

Typically, the distal end of the first threaded element is configured to remain proximal to the stopper, or proximal to a distal end of the stopper, and the proximal end of the second threaded element is configured to remain proximal to the distal end of the stopper at all times during the rotating of the first threaded element.

Typically, the apparatus comprises a housing base, the vial and the threaded elements being configured to be inserted into or otherwise coupled to the housing base. For some applications, a portion of the housing base is configured to automatically displace the threaded elements and the stopper toward a distal end of the vial during the insertion into the housing base.

In some embodiments, the subject couples a housing top to the housing base after the vial is inserted into the housing base. The housing top typically contains a motor and a cog, the motor configured to rotate the cog and the cog configured to rotate the first threaded element. For some applications, a control unit administers a basal rate of the substance to the subject by controlling the motor. Alternatively or additionally, the control unit is configured to receive an input and to administer a bolus of the substance to the subject responsively to the input. Further alternatively or additionally, the control unit controls the administering of the substance to the subject in response to the detection by a sensor of one or more physiological parameters of the subject.

For some applications, the substance is administered to the subject via a cannula. Typically, the cannula surrounds a needle. The cannula is inserted into the subjects skin by piercing the subject's skin with the needle and inserting the needle. The needle is typically retracted from the subject's skin following the piercing and the cannula remains inserted in the subject's skin for the duration of the time that the substance is administered to the subject.

In some applications, the apparatus comprises a skin-piercing activation mechanism. Piercing the subject's skin comprises rapidly piercing the subject's skin by displacing a force-receiving element of an activation mechanism. The application of a force to the activation mechanism that exceeds a threshold force displaces the force-receiving element. For example, the subject may press a button coupled to the housing base or top, and, upon application of force that exceeds the threshold force, the needle is suddenly released, and rapidly pierces the skin.

It is noted that the use of two separate portions, the housing top and the housing base, facilitates easier sterilization of components that should be sterilized—particularly the tissue-contacting components of the housing base. The housing top, which typically comprises the battery, motor, and associated electronics, is not typically sterilized.

Additionally, for added convenience of use by the subject, the housing top may be easily removed prior to showering. Alternatively or additionally, all of the components in the housing top are waterproof, such that the housing top may remain coupled to the housing bottom while the subject showers.

In some embodiments, the vial comprises (for example, the vial may be composed of) a cyclic olefin polymer, such as Crystal Zenith®.

There is therefore provided, in accordance with an embodiment of the present invention, apparatus for administering a substance to a subject, including: a vial that contains the substance; a stopper within the vial, slidably coupled to the vial; a first threaded element (a) rotatable with respect to the vial and (b) substantially immobile proximally with respect to the vial during rotation of the first threaded element; and a second threaded element that is threadedly coupled to the first threaded element, at least a distal end of the second threaded element substantially non-rotatable with respect to the vial, the distal end of the second threaded element defining a coupling portion that couples the second threaded element to the stopper, and the first threaded element, by rotating, linearly advancing the stopper and at least the distal end of the second threaded element toward a distal end of the vial.

In an embodiment, the apparatus further includes: a vial housing unit that houses the vial and the threaded elements; a needle housing unit coupled to the vial housing unit and not rigidly connected to the housing unit; a needle housed within the needle housing unit; and a cannula at least partially disposed around the needle, and the apparatus is configured to administer the substance to the subject via the cannula.

In an embodiment, the distal end of the second threaded element is disposed at least partially within the stopper.

In an embodiment, the second threaded element is configured to be coupled to the stopper by a user.

In an embodiment, the second threaded element is provided to a user, the second threaded element already coupled to the stopper.

In an embodiment, the vial includes a circular barrel having an inner surface that is smooth.

In an embodiment, the substance includes insulin and the insulin is disposed within the vial.

In an embodiment, a distal end of the first threaded element remains proximal to a proximal end of the stopper at all times during the rotating of the first threaded element.

In an embodiment, the apparatus further includes a dividing stopper within the vial, slidably coupled to the vial; the vial includes a distal compartment and a proximal compartment, the distal compartment containing a powder and the proximal compartment containing a liquid, the dividing stopper reversibly inhibiting fluid communication between the distal compartment and the proximal compartment, and the first threaded element, by rotating, mixes the powder and the liquid by advancing the dividing stopper toward the distal end of the vial.

In an embodiment, a distal end of the second threaded element is configured to remain proximal to a distal end of the stopper at all times during the rotating of the first threaded element.

In an embodiment, the apparatus further includes a housing base, the vial and the first and second threaded elements are configured to be inserted into the housing base, and a portion of the housing base is configured to impede proximal linear motion of the first threaded element during rotation of the first threaded element.

In an embodiment, the first threaded element includes thread that defines a maximal diameter and a pitch, and a ratio between the maximal diameter and the pitch is 6:1 to 15:1.

In an embodiment, friction between the stopper and an inner surface of the vial impedes rotation of the second threaded element.

In an embodiment, friction between the stopper and an inner surface of the vial impedes rotation of the second threaded element while allowing distal motion of the second threaded element.

In an embodiment, the apparatus further includes a housing base, the vial and the first and second threaded elements are configured to be inserted into the housing base, and a portion of the housing base is configured to displace the threaded elements and the stopper toward the distal end of the vial during the insertion into the housing base.

In an embodiment, the portion of the housing base is configured to apply a sufficient force, in displacing the threaded elements and the stopper, to overcome friction between the stopper and the vial that is due to prolonged storage of the stopper in contact with the vial.

In an embodiment, the apparatus further includes a cannula coupled to the housing base and configured to be inserted into skin of the subject, and the housing base, by displacing the threaded elements and the stopper, is configured to expel gas through a distal end of the cannula.

In an embodiment, the portion of the housing base, by displacing the threaded elements and the stopper, is configured to expel at least some of the substance through the distal end of the cannula.

In an embodiment, the portion of the housing base is disposed with respect to a portion at a proximal end of the vial such that, during the insertion of the vial and the threaded elements into the housing base, relative motion between the portion of the housing base and the portion at the proximal end of the vial displaces the threaded elements and the stopper toward the distal end of the vial.

In an embodiment, the portion of the housing base is disposed such that sliding motion between the portion of the housing base and the portion at the proximal end of the vial advances the threaded elements and the stopper toward the distal end of the vial.

In an embodiment, the apparatus further includes: at least one cog that is couplable to a proximal end of the first threaded element and configured to rotate the first threaded element by rotating; a motor configured to rotate the cog; and a housing top, to which the cog and the motor are coupled.

In an embodiment, the apparatus further includes a control unit coupled to the motor, and the control unit is configured to receive a coded indication of a characteristic of the substance, and to control the motor in response to the indication of the characteristic of the sub stance.

In an embodiment, the apparatus further includes a control unit coupled to the motor, and the control unit is programmable and is configured to be programmed to administer a basal rate of the substance to the subject by controlling the motor.

In an embodiment, the apparatus further includes a control unit coupled to the motor, and the control unit is configured to receive an input and to administer a bolus of the substance to the subject responsively to the input.

In an embodiment, the apparatus further includes: a control unit coupled to the motor; and a sensor configured to detect a physiological parameter of the subject and to transmit a signal to the control unit responsively to the parameter, and the control unit is configured to control the motor responsively to the signal.

In an embodiment, the sensor is configured to be implanted in the subject's body.

In an embodiment, the sensor is configured to transmit the signal wirelessly.

In an embodiment, the apparatus further includes a housing base configured to hold the vial, and the housing base and the housing top are configured to be coupled together by the subject prior to the administering of the substance, and decoupled from each other by the subject following the administering of the substance.

In an embodiment, the housing top is configured to be reused subsequent to the administering of the substance from the vial, and the housing base and the threaded elements are configured to be discarded subsequent to the administering of the substance from the vial.

In an embodiment, the apparatus further includes: one or more magnetic elements coupled to the housing base; and one or more magnetic elements coupled to the housing top, and the magnetic elements are configured to reversibly magnetically couple the housing base to the housing top when the housing base and housing top are aligned.

In an embodiment, the apparatus further includes: a housing base, and the vial and the threaded elements are configured to be inserted into the housing base; a needle coupled to the housing base; and a cannula at least partially disposed around the needle, the needle is configured to pierce skin of the subject and insert the cannula into the subject's skin, the needle is configured to retract subsequent to piercing, and the apparatus is configured to administer the substance to the subject via the cannula.

In an embodiment, the apparatus further includes a needle activation mechanism coupled to the needle, the needle activation mechanism including: a subject-contact surface for application thereto of a force by the subject; and a force-receiving element which is configured to be displaced when the force applied by the subject to the subject-contact surface exceeds a threshold force, and the needle is configured to rapidly pierce the skin in response to displacement of the force-receiving element due to the force exceeding the threshold force.

In an embodiment, the apparatus further includes a spring, and the spring is configured to retract the needle subsequent to the piercing.

In an embodiment, the apparatus further includes: a housing base, the vial and the threaded elements being configured to be inserted into the housing base; and a needle coupled to the housing base and configured to pierce skin of the subject, and the apparatus is configured to administer the substance to the subject via the needle.

In an embodiment, the apparatus is configured to administer substantially all of the substance in less than one hour.

In an embodiment, the substance includes glatiramer acetate and the apparatus is configured to deliver the glatiramer acetate to the subject via the needle.

In an embodiment, the apparatus further includes: a housing base, the vial and the threaded elements being configured to be inserted into the housing base; and a plurality of microneedles coupled to the housing base and configured to pierce skin of the subject, and the apparatus is configured to administer the substance to the subject via the plurality of microneedles.

In an embodiment, a diameter of each of the microneedles is less than 150 microns.

In an embodiment, the first threaded element includes a screw, and the second threaded element includes a nut disposed at least partially around the screw.

In an embodiment, the screw includes a telescopic screw, and the screw is configured to advance a distal end of the nut toward the distal end of the vial by extending the telescopic screw toward the distal end of the vial.

In an embodiment, the telescopic screw includes two at least partially overlapping portions.

In an embodiment, the telescopic screw includes three or more at least partially overlapping portions.

In an embodiment, the nut includes a telescopic nut, and the screw is configured to advance a distal end of the nut toward the distal end of the vial by extending the telescopic nut toward the distal end of the vial.

In an embodiment, the telescopic nut includes two at least partially overlapping portions.

In an embodiment, the telescopic nut includes three or more at least partially overlapping portions.

In an embodiment, the first threaded element includes a nut, and the second threaded element includes a screw disposed at least partially inside the nut.

In an embodiment, the screw includes a telescopic screw, and the nut is configured to advance a distal end of the screw toward the distal end of the vial by extending the telescopic screw toward the distal end of the vial.

In an embodiment, the telescopic screw includes two at least partially overlapping portions.

In an embodiment, the telescopic screw includes three or more at least partially overlapping portions.

In an embodiment, the nut includes a telescopic nut, and the nut is configured to advance a distal end of the screw toward the distal end of the vial by extending the telescopic nut toward the distal end of the vial.

In an embodiment, the telescopic nut includes two at least partially overlapping portions.

In an embodiment, the telescopic nut includes three or more at least partially overlapping portions.

There is additionally provided, in accordance with an embodiment of the present invention, a method, including: providing: a vial that contains a substance, and is sealed by a stopper, and first and second threaded elements for placement within the vial, the first and second threaded elements being threadedly coupled to each other, a distal end of the second threaded element being for coupling to the stopper; inserting the vial into a housing base, the threaded elements having been inserted into the vial, and the distal end of the second threaded element having been coupled to the stopper; and pushing the substance out of the vial by advancing the stopper and at least the distal end of the second threaded element toward a distal end of the vial, the advancing being performed by: rotating the first threaded element with respect to the vial, impeding proximal linear motion of the first threaded element with respect to the vial during rotation of the first threaded element, and impeding rotational motion of at least the distal end of the second threaded element with respect to the vial.

There is further provided, in accordance with an embodiment of the present invention, apparatus for administering a substance to a subject, including: a vial that contains the substance; a stopper within the vial, slidably coupled to the vial; a shaft within the vial, a distal portion of the shaft being coupled to the stopper; and a rotation mechanism disposed proximally to the vial, coupled to the shaft and configured to linearly advance the stopper toward a distal end of the vial by rotating the shaft, and at all times during the rotating of the shaft, (a) a distal end of the shaft is configured to remain proximal to a distal end of the stopper, and (b) a proximal end of the shaft is configured to remain distal to a proximal end of the rotation mechanism.

There is additionally provided, in accordance with an embodiment of the present invention, a method, including: providing a vial that contains a substance, is sealed by a stopper, and has therein a shaft that is coupled to the stopper; inserting the vial into a housing base, a rotation mechanism being coupled to the housing base proximally to the vial; pushing the substance out of the vial by advancing the stopper by rotating the shaft; maintaining a distal end of the shaft proximal to a distal end of the stopper at all times during the rotating of the shaft; and maintaining a proximal end of the shaft distal to a proximal end of the rotation mechanism at all times during the rotating of the shaft.

There is further provided, in accordance with an embodiment of the present invention, apparatus for administering a substance to a subject, including: a vial that contains the substance; a stopper within the vial, slidably coupled to the vial; a first threaded element (a) rotatable with respect to the vial and (b) substantially immobile proximally with respect to the vial during rotation of the first threaded element; and a second threaded element that is threadedly coupled to the first threaded element, at least a distal end of the second threaded element substantially non-rotatable with respect to the vial, the distal end of the second threaded element remaining proximal to a distal end of the stopper at all times during rotation of the first threaded element, and the first threaded element, by rotating, linearly advancing the stopper and at least the distal end of the second threaded element toward a distal end of the vial.

There is additionally provided, in accordance with an embodiment of the present invention, a method, including: providing: a vial that contains a substance, and is sealed by a stopper, and [0158] first and second threaded elements for placement within the vial, the first and second threaded elements being threadedly coupled to each other, a distal end of the second threaded element being for coupling to the stopper; inserting the vial into a housing base, the threaded elements having been inserted into the vial, and the distal end of the second threaded element having been coupled to the stopper; pushing the substance out of the vial by advancing the stopper and at least the distal end of the second threaded element toward a distal end of the vial, the advancing being performed by: rotating the first threaded element with respect to the vial, impeding proximal linear motion of the first threaded element with respect to the vial during rotation of the first threaded element, and impeding rotational motion of at least the distal end of the second threaded element with respect to the vial; and maintaining the distal end of the second threaded element proximal to a distal end of the stopper at all times during the rotating of the first threaded element.

BRIEF DESCRIPTION OF THE SEVERAL VIEWS OF THE DRAWINGS

The foregoing summary, as well as the following detailed description of a preferred embodiment of the invention, will be better understood when read in conjunction with the appended drawings. For the purpose of illustrating the invention, there are shown in the drawings an embodiment which is presently preferred. It should be understood, however, that the invention is not limited to the precise arrangements and instrumentalities shown.

In the drawings:

FIGS. 6A-D are schematic cross-sectional illustrations, taken along line VI of FIG. 5A, of the vial at respective stages of use of the apparatus, in accordance with an embodiment of the present invention;

FIG. 6E is a force vector diagram showing the forces acting on a stopper during operation of the apparatus, in accordance with an embodiment of the present invention;

FIGS. 9A-B are schematic illustrations of a double-chambered vial, in accordance with an embodiment of the present invention;

FIGS. 10A-B are schematic illustrations of a double-chambered vial, in accordance with an alternative embodiment of the present invention;

FIG. 11 is a schematic illustration of a vial, in accordance with an embodiment of the present invention;

FIGS. 12A-B are schematic illustrations of a vial containing a telescopic screw, in accordance with respective embodiments of the present invention;

FIG. 13 is a schematic illustration of a vial containing a telescopic nut, in accordance with an embodiment of the present invention; and FIG. 14 is a schematic illustration of apparatus including a vial housing unit and a separate needle housing unit, in accordance with an embodiment of the present invention.

DETAILED DESCRIPTION OF THE INVENTION

Figure 1A:
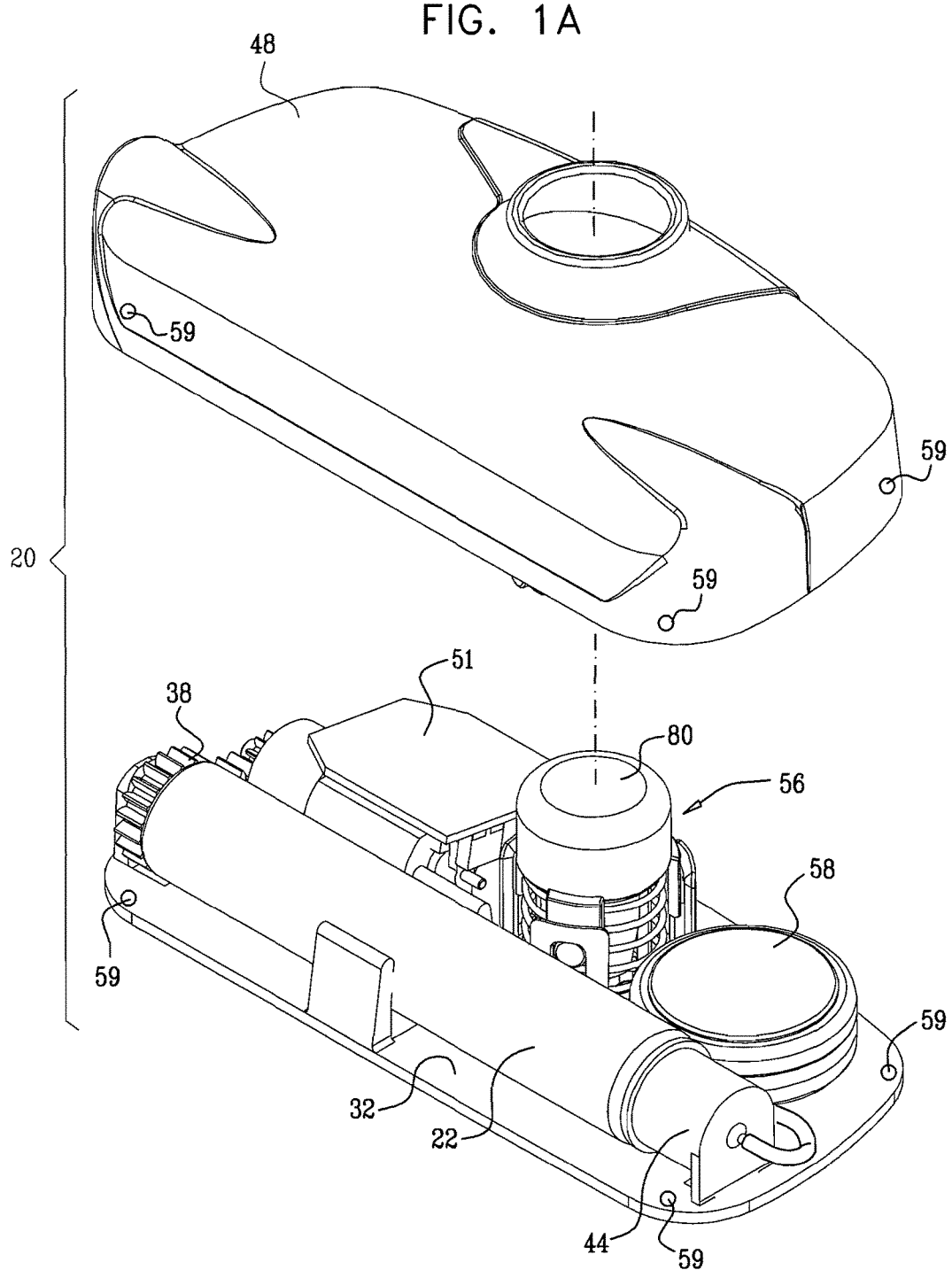
FIG. 1A is a schematic illustration of apparatus for administering a substance to a subject, in accordance with an embodiment of the present invention.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the device and designated parts thereof. Unless specifically set forth herein, the terms "a", "an" and "the" are not limited to one element but instead should be read as meaning "at least one". The terminology includes the words noted above, derivatives thereof and words of similar import.

Figure 1B:
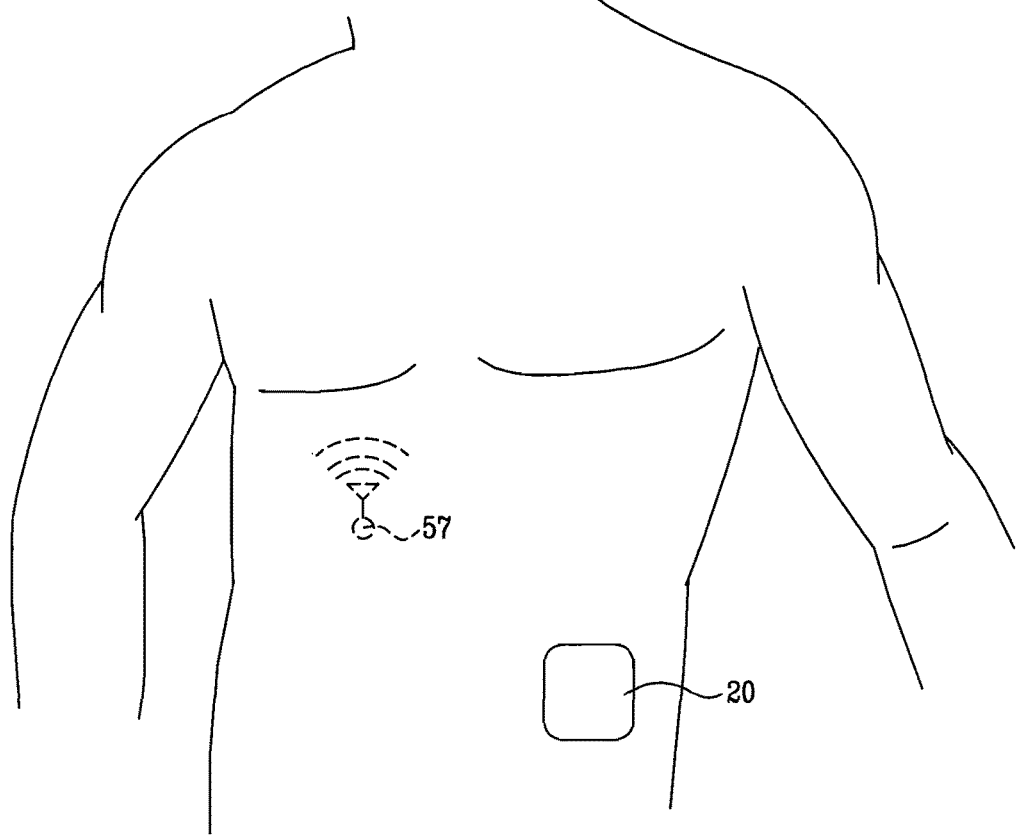
FIG. 1B is a schematic illustration of the apparatus of FIG. 1A on a subject's body, a sensor for use with the apparatus being disposed inside the subject's body, in accordance with an embodiment of the present invention.
Figure 2:
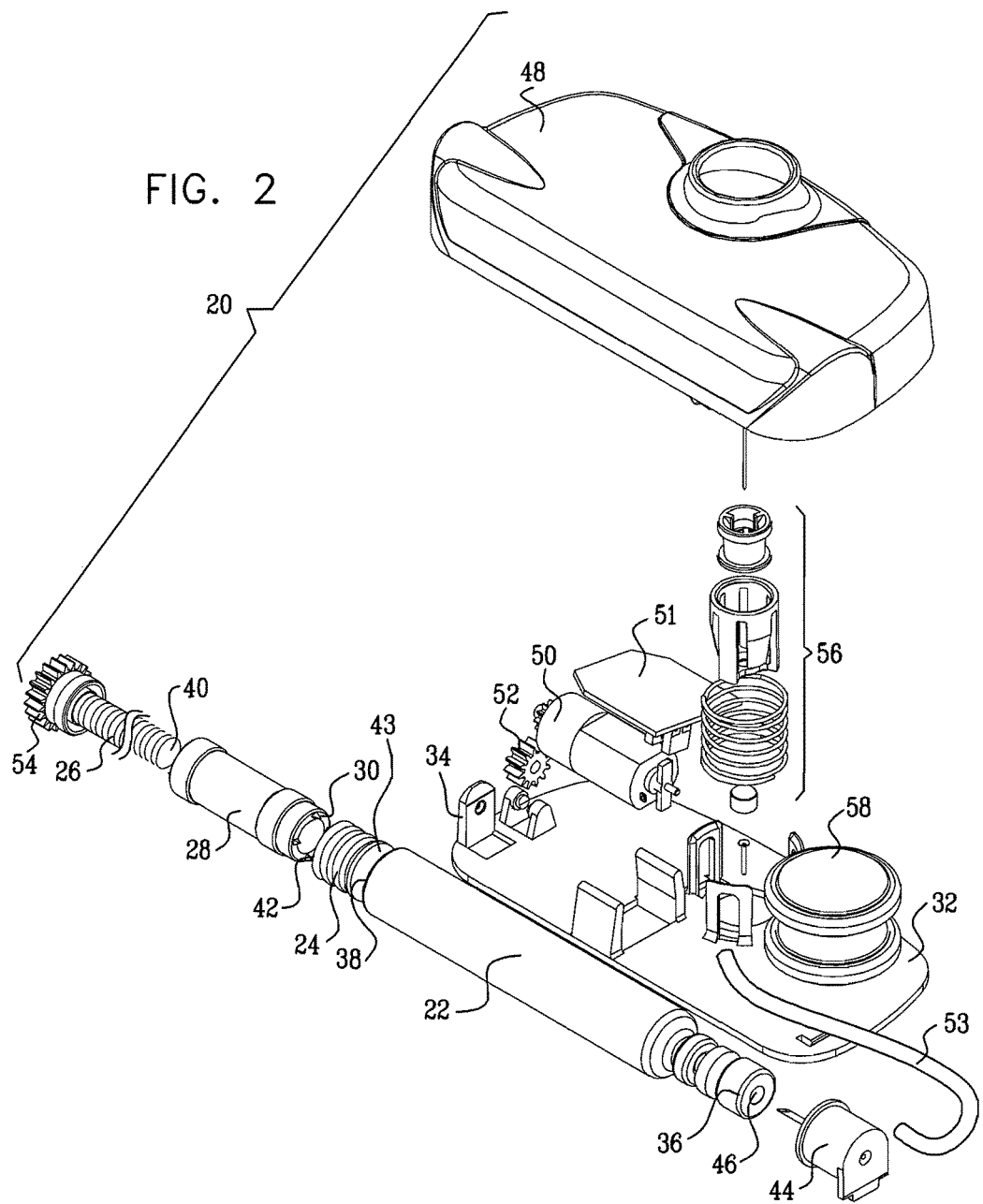
FIG. 2 is a schematic exploded view of the apparatus of FIG. 1, in accordance with an embodiment of the present invention.

Reference is now made to FIGS. 1A-B and 2, which are schematic illustrations of apparatus 20 for administering a substance, for example, insulin, to a subject, in accordance with an embodiment of the present invention. Typically, apparatus 20 comprises a vial 22 that contains the substance to be administered to a subject. Vial 22 is sealed at its proximal end by a stopper 24. A first threaded element 26 (e.g., a screw, as shown) is disposed at least in part within the vial, and a second threaded element 28 (e.g., a nut, as shown) is also disposed within the vial, threadedly coupled to the first threaded element. The distal end of the second threaded element defines a coupling portion 30 that couples the second threaded element to the stopper. The first threaded element is rotated by a rotation mechanism (e.g., motor 50), and by rotating, linearly advances the second threaded element and the stopper toward a distal end of the vial, without substantially rotating the second threaded element or the stopper.

In some embodiments, first threaded element 26 is a nut and second threaded element 28 is a screw disposed at least in part inside the nut. The nut is configured to rotate and to cause the screw and the stopper to advance toward a distal end of the vial due to the rotation of the nut. Alternatively, the first threaded element is a first screw and the second threaded element is a second screw. The first screw is configured, by rotating, to advance the second screw and the stopper toward the distal end of the vial. In general, apparatus 20 comprises a first threaded element that rotates, but is substantially immobile linearly during rotation of the first threaded element, and a second threaded element that (a) is substantially non-rotatable, (b) moves linearly toward the distal end of the vial in response to the rotation of the first threaded element, and (c) is coupled to the stopper. The first threaded element is rotated, causing the second threaded element and the stopper to advance distally.

Typically, vial 22 is inserted into a housing base 32. In some embodiments, portion 34 of the housing base is configured to impede proximal linear motion of first threaded element 26. (In the context of the present patent application and in the claims, the term "proximal" denotes a position toward an end 38 of the vial. The term "distal" denotes a position toward an end 36 of the vial, out of which the substance is administered to the subject.) In some embodiments, during rotation of first threaded element 26, stopper 24 is configured to impede rotation of second threaded element 28. Typically, friction of the stopper against the inside of the vial impedes rotational motion of the stopper, and element 28 being coupled to the stopper is similarly impeded. Thus, as first threaded element 26 is rotated, second threaded element 28 and the stopper advance linearly toward distal end 36 of the vial. In some embodiments, a standard, commercially-available vial and stopper are used as vial 22 and stopper 24. For some applications, the first and second threaded elements are standard, commercially-available threaded elements, e.g., a standard commercially-available screw and nut. Friction between the stopper and the vial impedes rotation of the stopper, while allowing distal movement of the stopper within the vial, as described in further detail herein below, with reference to FIGS. 6C and 6E.

For some applications, rotation of the second threaded element is impeded by other means, for example, as described herein below.

For some applications, the initial position of stopper 24 in vial 22 is in accordance with the amount of the substance that is contained within the vial and that is to be administered to the subject. The lengths of first and second threaded elements 26 and 28 are typically such that when the threaded portions of the elements are maximally overlapping (i.e., fully screwed together), and the elements are disposed within the vial, coupling portion 30 couples the second threaded element to the stopper. For example, the lengths of the screw and the nut, shown in FIG. 2, are typically such that when the screw is maximally inserted within the nut, and the screw and nut are disposed within the vial, coupling portion 30 of the nut couples the nut to the stopper. For example, if the vial contains a small amount of the substance prior to administering the substance, then stopper is disposed toward distal end 36 of the vial. In such a case, a relatively long screw/nut assembly (or screw/screw assembly) is designated to be disposed within the vial, so that coupling portion 30 couples the nut to the stopper. If, on the other hand, a large volume of the substance is contained within the vial, then a relatively short screw/nut assembly (or screw/screw assembly) is typically disposed within the vial. For some applications, screw/nut assemblies (or screw/screw assemblies) are color-coded or otherwise marked to indicate which screw/nut assembly (or screw/screw assembly) is suitable for use with which initial volume of substance.

In an alternative embodiment, first and second threaded elements 26 and 28 are placed in the vial, without being selected based on the initial volume of substance, and the elements are unscrewed from each other a suitable amount in order to facilitate the coupling of coupling portion 30 to the stopper.

Typically, a distal end 40 of the first threaded element 26 is configured to remain proximal to the stopper, or proximal to distal end 43 of the stopper, at all times during the rotating of the first threaded element. Further typically, the distal end of the second threaded element remains proximal to the distal end of the stopper at all times during the rotation of the first threaded element. The stopper typically provides a seal between a first portion of the vial, which is distal to the stopper, and a second portion of the vial, which is proximal to the stopper. In some embodiments, the sterility of the substance disposed in the first portion is maintained by the stopper providing a seal between the first portion and the second portion, threaded elements being disposed in the second portion. The first and second threaded elements assembly may be viewed as a shaft that converts the rotational motion of motor 50 to distal advancement of stopper 24. Typically, at all times during the rotating of the shaft, (a) the distal end of the shaft (i.e., the distal end of the second threaded element) is configured to remain proximal to a distal end of the stopper, and (b) the proximal end of the shaft (i.e., the proximal end of the first threaded element) is configured to remain distal to a proximal end of the rotation mechanism.

For some applications, a vial piercing mechanism 44 is movably (e.g., rotatably) coupled to housing base 32. As part of the insertion of vial 22 into the housing base, a seal 46 at distal end 36 of the vial is pierced by pressing the seal against the piercing mechanism. The substance is configured to subsequently flow through a tube 53 toward an activation mechanism 56, which is typically coupled to the housing base, and is configured to insert a cannula and/or a needle through the subject's skin and to deliver the substance via the cannula and/or the needle.

Although first and second threaded elements 26 and 28 have been described as being within vial 22 (e.g., the apparatus may be bought by the subject with the threaded elements already within the vial), in some embodiments, the threaded elements are inserted into the vial and are coupled to stopper 24 by the subject and/or by a healthcare provider. In some embodiments, vial 22 and stopper 24 are a standard, commercially-available vial and stopper, for example, the vial may be a circular barrel with a smooth inner wall. The first and second threaded elements are inserted into the vial and coupled to the stopper, and the apparatus dispenses the substance, in accordance with the techniques described hereinabove. The friction between the standard stopper and the standard vial prevent the second threaded element from rotating due to the coupling of the second threaded element to the stopper, as described hereinabove. For some applications, providing the apparatus described herein for use with standard, commercially-available vials and stoppers provides a commercial advantage.

For some applications, the threaded elements are coupled to housing base 32, and the subject and/or a healthcare provider moves the vial with respect to the housing base in order to couple the stopper to the second threaded element. For example, a standard, commercially-available vial and stopper may be moved with respect to the housing base, in order to couple the stopper to the second threaded element, the threaded elements being coupled to the housing base.

In some embodiments, a housing top 48 is coupled by the subject to housing base 32. The housing top typically comprises a motor 50 and a battery 58. (In an embodiment, the battery is coupled to housing base 32.) For some applications, a first cog 52 (i.e., a motor cog) is coupled to housing base 32. The motor is configured to rotate the first cog 52, and the first cog 52 is configured to rotate first threaded element 26. Typically, first cog 52 engages a second cog 54, the second cog 54 being coupled to the proximal end of threaded element 26, and/or comprising the proximal portion of threaded element 26. In some embodiments, only a single cog is used, the single cog being coupled to and/or comprising a proximal portion of threaded element 26, and the single cog being rotated directly by the motor. Alternatively or additionally, other techniques known in the art are used for converting motion from a motor to rotational or linear motion.

For some applications, the subject reversibly couples the housing top to housing base 32. Following the termination of the delivery of the substance to the subject from vial 22, the subject and/or a healthcare provider decouples the housing top from the housing base. In some embodiments, the housing top is configured to be re-used with another housing base, and the housing base is configured to be discarded after a single use. For some applications, the housing top and the housing base comprise magnetic materials 59 that are configured to releasably couple the housing top to the housing base when the top and the base are aligned.

For some applications, a control unit 51 is coupled to motor 50. In some embodiments, the control unit administers a basal rate of the substance to the subject by controlling the motor. Alternatively or additionally, the control unit is configured to receive an input and to administer a bolus of the substance to the subject responsively to the input. For example, housing top 48 may comprise two buttons. When both buttons are pressed at the same time, the control unit is configured to administer a bolus of the drug. Alternatively, a button 80 associated with activation mechanism 56 may be configured to cause the control unit to administer a bolus of the drug, when pushed subsequent to the insertion mechanism having been activated. Further alternatively or additionally, a sensor 57 (shown in FIG. 1B) is configured to detect one or more physiological parameters of the subject. The control unit is configured to control the administering of the substance in response to the detected parameters. In some embodiments, the sensor is configured to be implanted in the subject. For some applications, the sensor transmits the detected parameters to the control unit wirelessly.

In some embodiments, vial 22 has a distal compartment which contains a powder, and a proximal compartment which contains a liquid. The distal compartment and the proximal compartment are reversibly separated by a dividing stopper 134 (shown in FIGS. 9A-B). First threaded element 26, by rotating, causes the powder and the liquid to mix by advancing the dividing stopper toward distal end 36 of the vial, as described in detail herein below, with reference to FIGS. 9A-B.

Figure 3:
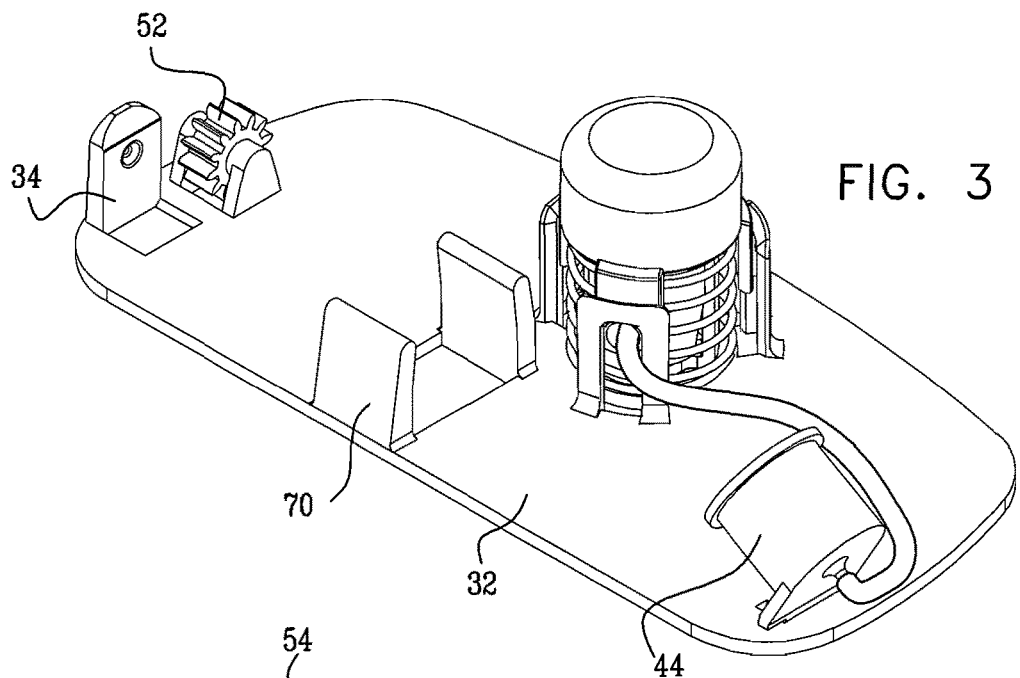
FIG. 3 is a schematic illustration of a housing base of the apparatus of FIG. 1, in accordance with an embodiment of the present invention.
Figure 4:
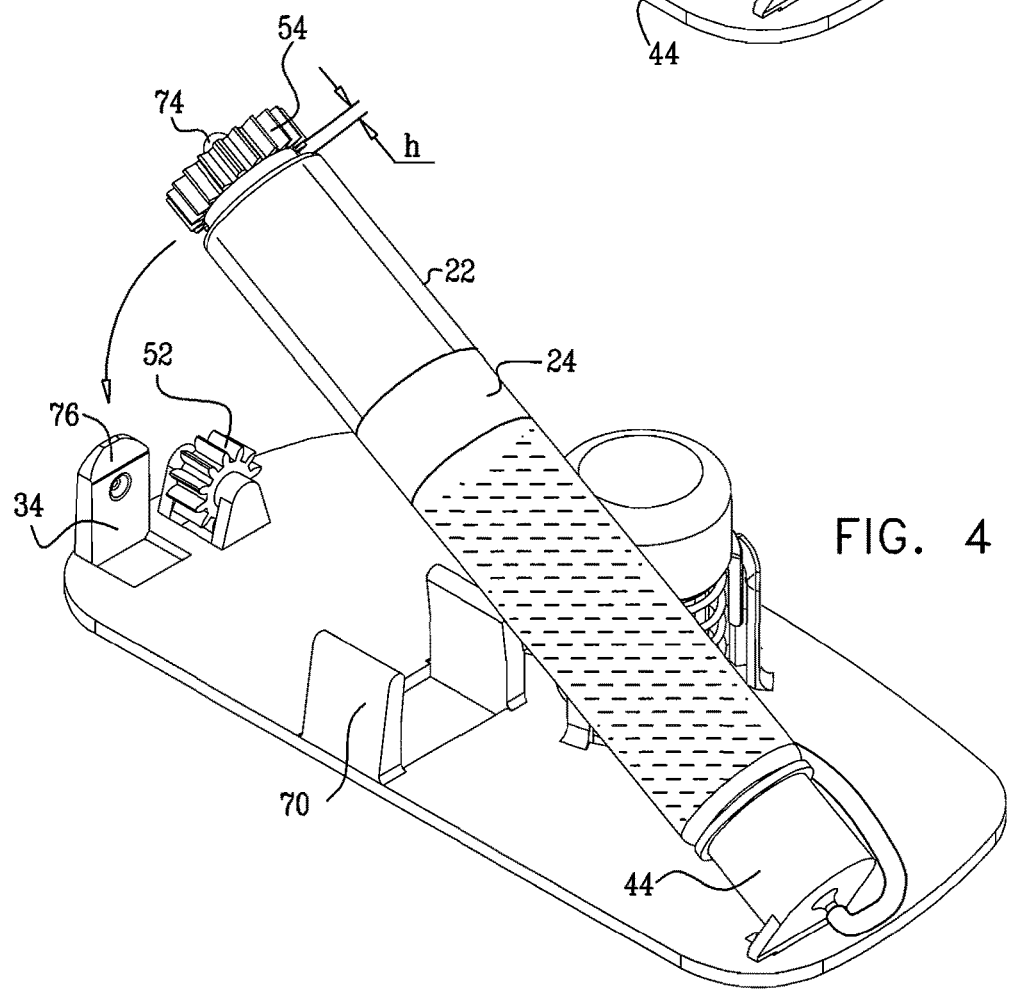
FIG. 4 is a schematic illustration of a vial being inserted into the housing base of FIG. 3, in accordance with an embodiment of the present invention.

Reference is now made to FIGS. 3 and 4, which are respectively a schematic illustration of housing base 32, and a schematic illustration of vial 22 being inserted into the housing base, in accordance with an embodiment of the present invention. The housing base, as shown in FIG. 3, is prepared for the insertion of vial 22. The distal end of the vial is inserted into vial piercing mechanism 44, which pierces the seal at the distal end of the vial. The vial is then lowered into the housing base. Typically, opposing resilient arms 70 support the vial upon the housing base.

In some embodiments, as vial 22 is lowered into housing base 32, first cog 52 engages second cog 54. For some applications, as the vial is lowered, portion 34 of the housing base automatically displaces first and second threaded elements 26 and 28 (and therefore stopper 24) toward distal end 36 of the vial. In some embodiments, the stopper is disposed within the vial such that before the insertion of the vial into the housing, first threaded element 26 protrudes a distance h from the proximal end of the vial. The proximal end of the first threaded element (or of second cog 54) comprises a rounded portion 74. Portion 34 of the housing base comprises an angled face 76. As rounded portion 74 slides past the angled face, the first threaded element is pushed the distance h inside the vial. As a result, the threaded elements and the stopper are displaced toward the distal end of the vial.

In some embodiments, apparatus 20 comprises alternative means of pushing threaded elements 26 and 28 inside vial 22 during the insertion of the vial into housing base 32. For example, the proximal end of first threaded element 26 may comprise an angled face and portion 34 of the housing base may comprise a rounded portion. Alternatively, both the proximal end of the first threaded element and portion 34 of the housing may comprise an angled face and/or a rounded portion.

Figure 7A:
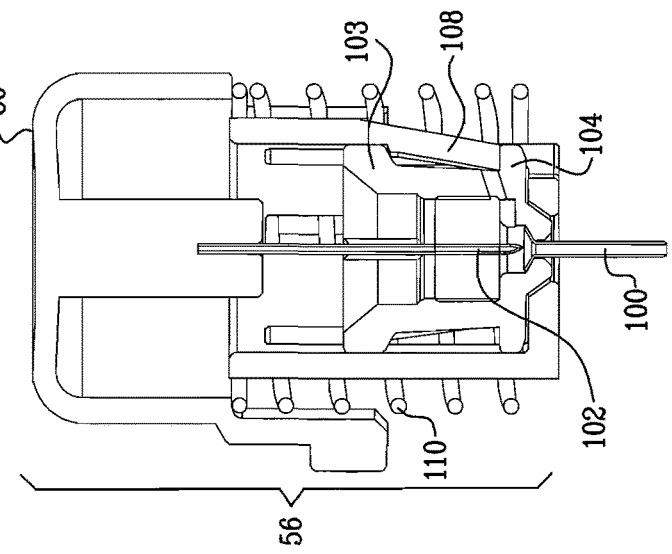
FIGS. 7A-C are schematic cross-sectional illustrations, taken along line VII of FIG. 5A, of an activation mechanism of the apparatus at respective stages of operation of the apparatus, in accordance with an embodiment of the present invention.
Figure 7B:
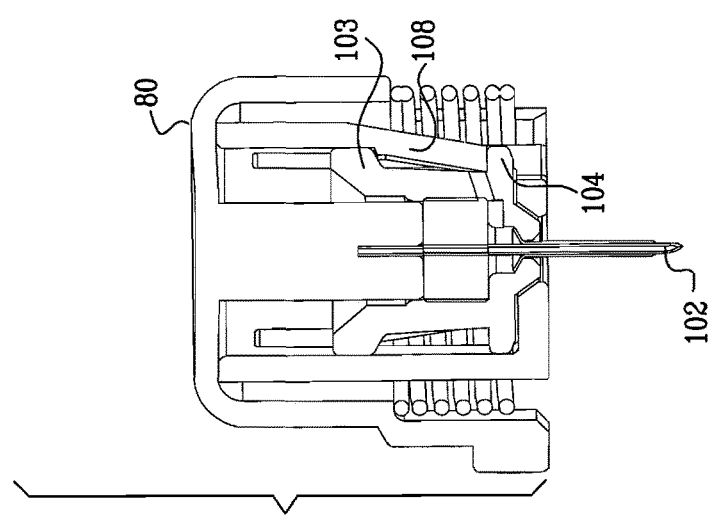
Figure 7C:
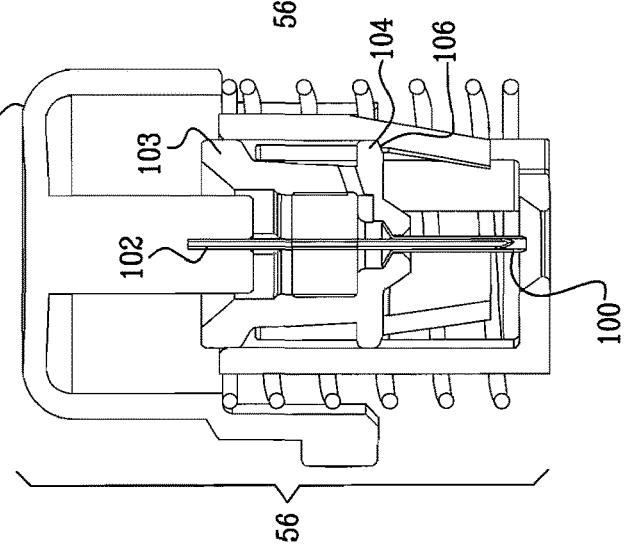

For some applications, portion 34 of housing base 32 is configured to apply a sufficient force, in displacing threaded elements 26 and 28 and stopper 24, to overcome friction between stopper 24 and vial 22 that is due to prolonged storage of the stopper in contact with the vial. For example, the stopper may have been stored in contact with the inner surface of the vial for a period of at least one week or longer, as a result of which the stopper may have a higher effective static friction than would have existed if the stopper had been recently moved with respect to the vial. Alternatively or additionally, apparatus 20 comprises a cannula 100 and/or a needle 102 (as shown in FIGS. 7A-C), configured to be inserted in the subject's skin. Portion 34 of the housing base, by displacing the threaded elements and the stopper, is configured to expel gas through a distal end of the cannula and/or needle. In some embodiments, in addition to expelling the gas, portion 34 is configured to expel at least some of the substance therefrom, as a result of displacing the threaded elements and the stopper. Typically, the expelling of the substance from the distal end of the cannula before the cannula is inserted into the subject's skin increases the accuracy of the first dosage administered, because the initial activation of the motor essentially immediately administers the substance, without previously ejecting gas stored in the vial or conduits of apparatus 20.

Figure 5A:
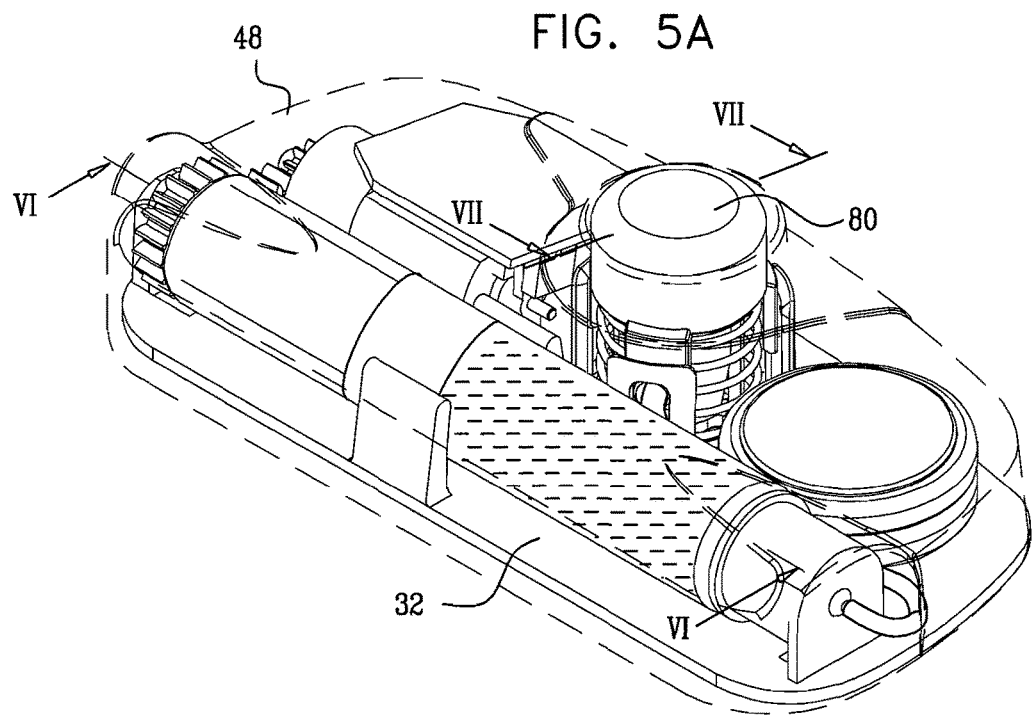
FIG. 5A is a schematic illustration of a vial inserted in the housing base, in accordance with an embodiment of the present invention.
Figure 5B:
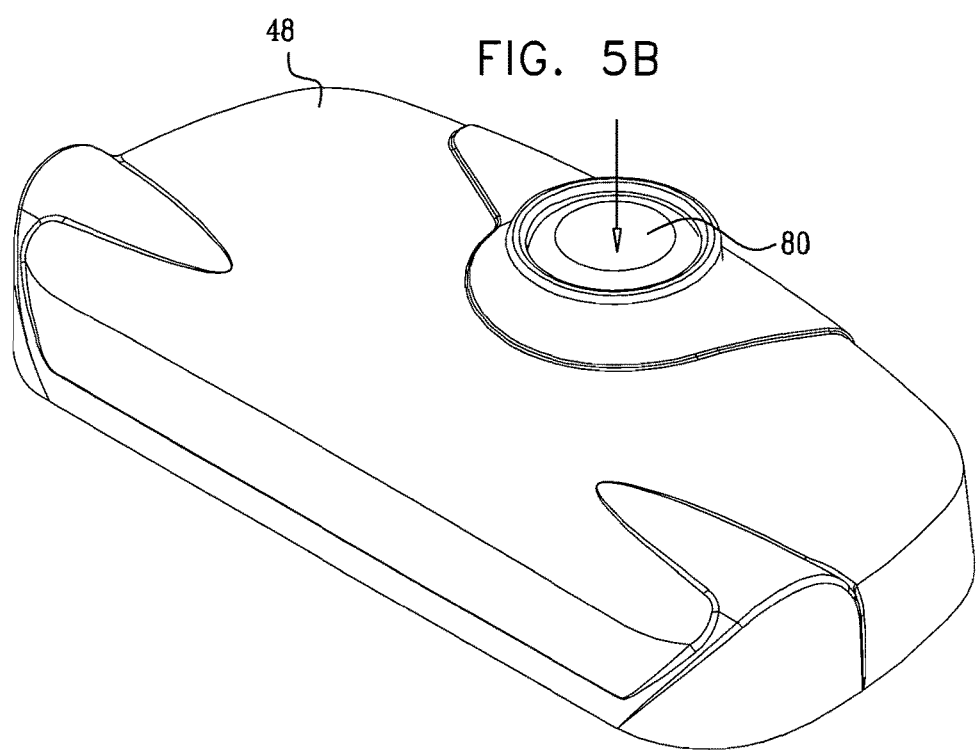
FIG. 5B is a schematic illustration of a housing top coupled to the housing base, in accordance with an embodiment of the present invention.

Reference is now made to FIGS. 5A and 5B, which are respectively a schematic illustration of vial 22 inserted in housing base 32, and of housing top 48 coupled to housing base 32, in accordance with an embodiment of the present invention. Housing top 48 is shaped such that when it is coupled to the housing base, button 80 of activation mechanism 56 is accessible to be pressed by the subject.

Reference is now made to FIGS. 6A-E. FIGS. 6A-D are schematic cross-sectional illustrations of vial 22 at respective stages of use of apparatus 20, in accordance with an embodiment of the present invention. FIG. 6E is a force vector diagram showing the forces acting on stopper 24 during rotation of first threaded element 26, in accordance with an embodiment of the present invention.

FIG. 6A shows vial 22 before its insertion into housing base 32. First threaded element 26 (e.g., a screw, as shown) protrudes by distance h from proximal end 38 of the vial. Second threaded element 28 (e.g., a nut, as shown) is threadedly coupled to the first threaded element and is coupled to stopper 24 via coupling portion 30. For example, coupling portion 30 may be shaped to define teeth 90, which are inserted into the stopper. Or, coupling portion 30 may be a flat surface that is flush with a proximal end 42 of stopper 24, or that is otherwise in contact with the stopper.

During insertion of the vial into the housing base, the first and second threaded elements and the stopper are displaced toward distal end 36 of the vial, as shown in FIG. 6B.

First threaded element 26 rotates during administration of the substance to the subject. Rotational motion of second threaded element 28 is impeded (even if not necessarily eliminated) by stopper 24 to which the second threaded element is coupled, and/or rotational motion of the second threaded element is impeded by alternative means, for example, as described with reference to FIGS. 8A-B. Additionally, proximal linear motion of the first threaded element with respect to the vial is impeded (by portion 34 of housing base 32, not shown) during rotation of the first threaded element. The rotation of the first threaded element combined with the impeded rotation of the second threaded element results in the second threaded element and the stopper advancing toward distal end 36 of vial 22, as shown in FIGS. 6C and 6D.

Typically, due to the rotation of the first threaded element, a linear force FL and a rotational force FR act on stopper 24, as shown in FIG. 6E. A linear friction force FFL between the stopper and vial 22 acts to oppose the linear advancement of the stopper, and a rotational friction force FFR between the stopper and the vial acts to oppose rotation of the stopper. Further typically, and as described in detail in the following paragraphs, friction between the stopper and the vial acts to oppose rotation of the stopper to a greater extent than it acts to oppose linear advancement of the stopper through the vial. In particular, in this embodiment, rotation of the stopper by (for example) a full rotation is impeded to a much greater extent than forward motion of the stopper by the pitch of the threaded elements is impeded, because significantly more friction must be overcome to produce a full rotation of the stopper than would need to be overcome in order for the stopper to advance the distance of the pitch of the threaded elements. As a result, friction generally acts to impede rotation of the stopper, while allowing distal movement of the stopper within the vial.

In a more detailed analysis of this effect, it is noted that, in some embodiments, friction between the stopper and the vial has the aforementioned effect due to selection of a suitable ratio of (a) the maximal diameter D of the first threaded element (shown in FIG. 6C) to (b) the pitch P of the first threaded element. Typically, the ratio of the maximal diameter D to the pitch P is 3:1 to 30:1, for example, 6:1 to 20:1, or 8:1 to 15:1. In some embodiments, the ratio is 6:1 to 15:1, for example, 10:1. The pitch of the second threaded element is equal to the pitch of the first threaded element. Proximal linear motion of the first threaded element is impeded (as described hereinabove). Therefore, when the first threaded element rotates and the second threaded element unscrews from the first threaded element, the second threaded element must either rotate, advance distally, or both rotate and advance distally.

By way of example, the first threaded element may have a maximal diameter of 8 mm and a pitch of 1 mm (i.e., a ratio of maximal diameter to pitch of 8:1). Accordingly, the outer perimeter of the first threaded element is greater than 25 mm (pi multiplied by the maximal diameter). As the first threaded element rotates through 360 degrees, if the second threaded element were to unscrew from the first threaded element by rotating, the second threaded element would rotate through a distance of more than 25 mm, around the perimeter of the first threaded element. Accordingly, the outer surface of the stopper would rotate in contact with the inner surface of the vial through an even greater distance, such as 40 mm (since the outer diameter of the stopper is greater than that of the first threaded element, as seen, for example, in any of FIGS. 6A-D). Alternatively, if the second threaded element unscrews from the first threaded element by advancing linearly through the vial, it advances by a distance of 1 mm, i.e., by a distance that is equal to the pitch of the threaded elements. Accordingly, in the presence of significant, intentionally-generated friction, the stopper advances substantially only linearly (in contact with the inner surface of the vial) by a distance of 1 mm, while rotating only to a relatively small extent.

It is noted that in some embodiments, friction between the stopper and the vial acts to impede rotation of the stopper, while allowing distal movement of the stopper within the vial, generally irrespective of the ratio of the maximal diameter D to the pitch P of the first threaded element.

As disclosed hereinabove, in some embodiments, friction acts to impede rotation of the stopper, while allowing distal movement of the stopper within the vial, even when the apparatus disclosed herein is used in conjunction with standard, commercially-available vials, stoppers, and threaded elements.

Reference is now made to FIGS. 7A-C, which are schematic illustrations of activation mechanism 56 of apparatus 20 at respective stages of operation of the apparatus, in accordance with an embodiment of the present invention. Typically, following the insertion of vial 22 into housing base 32, and the coupling of housing top 48 to the housing base, the bottom surface of the housing base is adhered to the subject's skin (e.g., with an adhesive), as shown in FIG. 1B. Subsequently, the activation mechanism is activated.

FIG. 7A shows activation mechanism 56 before the activation mechanism has been activated. Needle 102 is disposed within the activation mechanism, and cannula 100 is disposed around the outside of the needle. When the bottom surface of housing base 32 is adhered to the subject's skin, the subject pushes button 80, which is accessible through housing top, as shown in FIG. 5B. Until the force of the pushing of the button exceeds a threshold force, friction between a protrusion 104 of a structural element 103 and force receiving element 106 prevents the button and the needle being pushed down. (Force receiving element 106 is typically a surface of a holding portion 108, described herein below.) When the button is pushed by the subject with a force that exceeds the threshold force, force receiving element 106 is suddenly and rapidly pushed aside by protrusion 104. Typically, by applying sufficient force to the button to overcome the resistive force of force receiving element 106, the subject applies a level of force which is sufficient to suddenly and rapidly insert the needle and cannula into the subject's skin. FIG. 7B shows the needle and cannula having been advanced due to button 80 having been pushed with a force that exceeds the threshold force.

The pushing of button 80 with sufficient force causes structural element 103 to advance toward the subject's skin. When the structural element arrives at the end of its travel, it is held in place by holding portion 108. For example, a proximal portion of protrusion 104 may be secured by a distally-directed force applied thereto by a distal portion of force receiving element 106, constituting holding portion 108, as shown in FIG. 7B. When the subject releases button 80, as shown in FIG. 7C, a spring 110 pushes the button up, which retracts needle 102 back inside housing base 32. Cannula 100 is coupled to structural element 103, which is held in place by holding portion 108. Therefore, the cannula remains inserted in the patient's skin. The substance is administered to the subject via the cannula.

In an alternative embodiment, the substance is administered to the subject via needle 102, the needle remaining inserted in the subject's skin for the duration of the administration. In such an embodiment, apparatus 20 is typically configured to administer substantially all of the substance to the subject in less than one hour. For example, Copaxone® (or another drug) may be administered to the subject in this manner over the course of approximately one half hour.

In some embodiments, needle 102 comprises a plurality of microneedles, which are inserted into the subject's skin, and the substance is administered to the subject via the microneedles. Typically, the diameter of each of the microneedles is about 50-150 microns, e.g., about 100 microns, and the length of each of the microneedles is about 200-1000 microns.

In an embodiment, control unit 51 is configured to receive an indication, on vial 22, first threaded element 26, second threaded element 28, or another element, that indicates a characteristic of the contents of vial 22. For example, a barcode, RFID, mechanical code, or other code may indicate to the control unit the type of pharmaceutical product in the vial, the quantity of the substance, or a dosage schedule for administration of the substance. Typically, when the subject first receives the vial, stopper 24 is already in place within the vial at the correct position for initiating delivery of the substance.

Figure 8A:
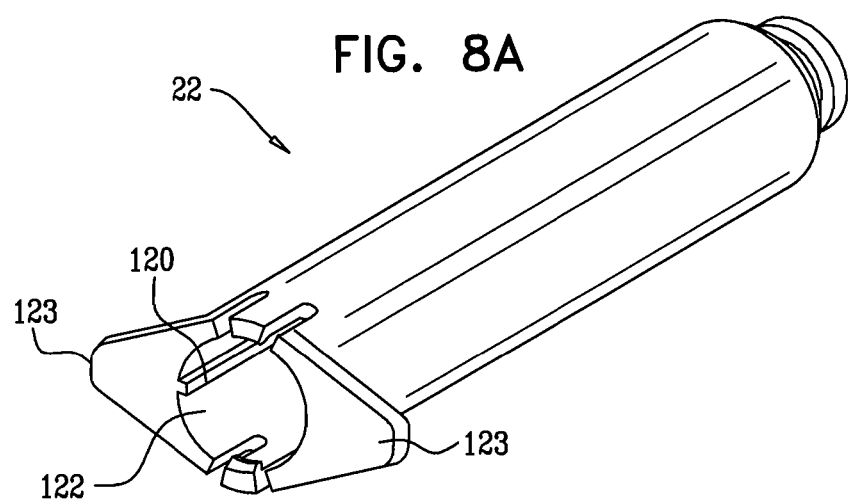
FIGS. 8A-B are schematic illustrations of a vial, in accordance with an embodiment of the present invention.
Figure 8B:
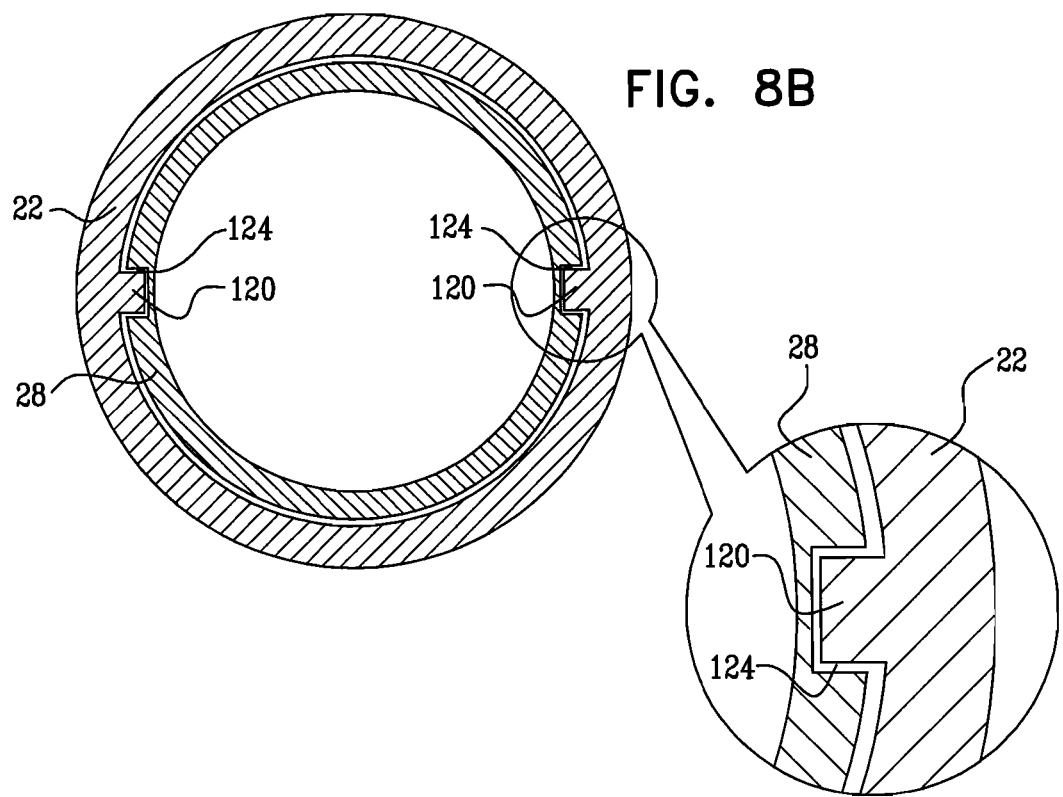

Reference is now made to FIGS. 8A-B, which are schematic illustrations of respective views of vial 22, in accordance with an embodiment of the present invention. For some applications, a protrusion 120 protrudes from inner surface 122 of the vial, and second threaded element 28 is a nut that is shaped to define a groove 124 on its outer surface. As the nut advances toward the distal end of the vial, groove 124 slides along protrusion 120, preventing the nut from rotating. Alternatively or additionally, stopper 24 is shaped to define a groove on its outer surface, the groove preventing the stopper, and therefore the second threaded element, from rotating. In some embodiments, inner surface 122 of vial 22 is not round, but, for example, is square, oval, or rectangular. The outer surface of the second threaded element, and/or the stopper, is shaped similarly to the inner surface of the vial. The shapes of inner surface 122, and the outer surface of the second threaded element and/or the stopper, prevent the second threaded element from rotating.

In some embodiments, vial 22 contains (for example, the vial may be composed of) a cyclic olefin polymer, such as Crystal Zenith®. In some embodiments, manufacturing the vial using a cyclic olefin polymer facilitates the molding of protrusion 120. For some applications, stopper 24 is coated with a fluoropolymer. Typically, using a vial that contains a cyclic olefin polymer, and/or a stopper that is coated with a fluoropolymer maintains the stability of a substance that is disposed within the vial. For example, the vial may be used to administer a monoclonal antibody to the subject, and the composition of the vial, the stopper, and/or the second threaded element may maintain the stability of the monoclonal antibody.

In some embodiments, the proximal end of vial 22 is shaped to define two or more flanges 123. Typically, the flanges facilitate the filling of the vial. For example, during the filling of the vial, the vial may be placed inside a hole of a tray, and the flanges may support the vial inside the hole. In some embodiments, the flanges are configured to hold the vial in a fixed position inside housing base 32.

Reference is now made to FIGS. 9A-B, which are schematic illustrations of vial 22, in accordance with an embodiment of the present invention. In some embodiments, the vial contains a distal compartment 130, and a proximal compartment 132, a dividing stopper 134 inhibiting fluid communication between the proximal and distal compartments. In some embodiments, a powder (for example, medication that is in the form of a powder) is disposed in distal compartment 130 and a liquid (e.g. water, saline, and/or a medication) is disposed in proximal compartment 132. As second threaded element 28 is advanced distally through the vial, dividing stopper 134 is advanced distally. The advancement of the dividing stopper exposes compartment 132 to conduit 136. As second threaded element 28 is further advanced, stopper 24 causes the liquid to flow into distal compartment 130 via the conduit, in the direction of arrow 138 (as shown in FIG. 9B). The liquid and the powder then mix and, for example, may form a solution or a suspension, before being administered to the subject. In some embodiments, a first liquid medication is disposed in distal compartment 130 and a second liquid medication is disposed in proximal compartment 132. Dividing stopper 134 inhibits fluid communication between the first and second medications. As second threaded element 28 advances through the vial, the two medications mix before being administered to the subject.

Reference is now made to FIGS. 10A-B, which are schematic illustrations of vial 22, in accordance with an embodiment of the present invention. The vial contains a distal compartment 130, and a proximal compartment 132, dividing stopper 134 inhibiting fluid communication between the proximal and distal compartments. In some embodiments, a medication is disposed in the distal compartment, and a flushing solution, such as water or saline, is disposed in the proximal compartment. As second threaded element 28 is advanced distally through the vial, dividing stopper 134 is advanced distally, thereby administering to the subject the medication disposed in proximal compartment 130. When dividing stopper 134 is advanced to a position toward distal end 36 of the vial the flushing solution flows through conduit 140 (in the direction of arrow 142) and flushes the medication from the vial and/or from conduits of apparatus 20.

It is noted that the term "providing" as used herein in the specification and in the claims, in the context of providing apparatus (for example, providing a vial), includes within its scope the apparatus being provided by the user of the apparatus, and is not limited to the sale of the apparatus.

Reference is now made to FIG. 11, which is a schematic illustration of vial 22, in accordance with an embodiment of the present invention. In some embodiments, first threaded element 26 is a nut that is rotatable with respect to vial 22. Second threaded element 28 is a screw that is threadedly coupled to the nut and disposed at least partially within the nut. During rotation of the nut, linear motion of the nut with respect to the vial is impeded (for example, by portion 34 of housing base 32, shown in FIG. 4). During rotation of the nut, the screw is substantially rotationally immobile with respect to the vial. Typically, the distal end of the screw is coupled to stopper 24 via coupling surface 30, and the stopper impedes rotation of the screw. Thus, during rotation of the nut, the screw and the stopper advance toward distal end 36 of the vial and administer the substance to the subject from the vial.

In some embodiments (as shown in FIG. 11), the distal end of the second threaded element is disposed inside stopper 24. Although FIG. 11 shows the distal end of a screw disposed inside the stopper, the scope of the present application includes having the distal end of any embodiment of the second threaded element disposed inside stopper 24, in accordance with any of the methods or apparatus described herein. For example, the second threaded element may be a nut, e.g., as shown in FIGS. 6A-D, the distal end of the nut being disposed inside the stopper instead of being coupled to the proximal end of the stopper, as shown in FIGS. 6A-D. Typically, using a second threaded element that is disposed inside the stopper facilitates the use of a vial having a shorter length than would be necessary if the second threaded element was not disposed inside the stopper.

Reference is now made to FIGS. 12A-B, which are schematic illustrations of vial 22 containing a telescopic screw 150, in accordance with an embodiment of the present invention. Vial 22 of FIG. 12 is generally similar to vial 22 described with reference to FIG. 11, except for differences described herein below.

In some embodiments, the second threaded element is a telescopic screw. First threaded element, by rotating, extends the telescopic screw and advances stopper 24 and distal end 152 of the telescopic screw toward distal end 36 of vial 22, in accordance with the techniques described hereinabove. In some embodiments, using a telescopic screw as the second threaded element facilitates the use of a smaller length vial to administer a given amount of the substance than would be necessary if a non-telescopic screw, or a nut were used as the second threaded element. In some embodiments, a telescopic screw is used as the first threaded element, and a nut is used as the second threaded element.

Although a telescopic screw having two overlapping portions 154 and 156 is shown, the scope of the present invention includes using a screw having more three or more overlapping portions as the second threaded element of vial 22. Typically, the ratio of the length of the telescopic screw when fully extended to the length of the telescopic screw when fully contracted (as shown in FIG. 12) is 1.5:1 to 2:1.

In some embodiments, as shown in FIG. 12B, a second threaded element (e.g., a nut or a screw) is used that is (a) telescopic, and (b) disposed at least partially inside stopper 24. For example, FIG. 12B shows a telescopic screw, a distal end of which is disposed inside stopper 24. Typically, using a second threaded element that is (a) telescopic, and (b) disposed at least partially inside stopper 24 facilitates the use of a shorter vial to administer a given amount of the substance than would otherwise be necessary, ceteris paribus.

Reference is now made to FIG. 13, which is a schematic illustration of vial 22 containing a telescopic nut 160, in accordance with an embodiment of the present invention. For some applications, a telescopic nut, such as that described in U.S. Pat. No. 6,905,298 to Haring, is used as the first threaded element (configuration not shown) or as the second threaded element (as shown) inside vial 22. In an embodiment, the nut is configured such that frictional forces between a first portion 164 and a second portion 166 of the nut prevent the first and second portion from becoming disengaged from each other. In addition, frictional forces between the screw and portion 166 prevent the screw and portion 166 from becoming disengaged. For example, the threads at the distal portion of the screw and on the inner surface of the proximal portion of portion 166 may widen, such that portion 166 cannot be unscrewed from the screw.

Vial 22 of FIG. 13 is generally similar to vial 22 described with reference to FIG. 12, except that a telescopic nut, instead of a telescopic screw, is used as the second threaded element. Although a telescopic nut having two overlapping portions 164 and 166 is shown, the scope of the present invention includes using a nut having three or more overlapping portions as the second threaded element of vial 22. Typically, the ratio of the length of the telescopic nut when fully extended to the length of the telescopic nut when fully contracted (as shown in FIG. 13) is 1.5:1 to 2:1.

Reference is now made to FIG. 14, which is a schematic illustration of apparatus 20 including a vial housing unit 170 and a separate needle housing unit 172, in accordance with an embodiment of the present invention. The apparatus shown in FIG. 14 is generally similar to the apparatus shown in FIGS. 1 and 2, except for the differences described herein below.

In some embodiments, activation mechanism 56 is housed in needle housing unit 172. The activation mechanism, as described hereinabove, inserts cannula 100 and/or needle 102 through the subject's skin and delivers the substance via the cannula and/or the needle. Vial 22 and control components, such as motor 50 and battery 58, are housed separately in vial housing unit 170. In some embodiments, needle housing unit 172 is adhered to the subjects skin, and vial housing unit 170 is not adhered to the subject's skin. Typically, the needle housing unit and the vial housing unit are not rigidly connected to each other. For example, vial housing unit 170 may be worn on the subject's belt, or elsewhere on the subject's clothing. Typically, vial housing unit 170 is coupled to needle housing unit 172 via tube 53, via which the substance flows from the vial toward activation mechanism 56.

It is noted that, although a specific configuration of activation mechanism 56 is shown, in some embodiments, needle housing unit 172 houses an activation mechanism having a different configuration. For example, needle housing unit 172 may house only cannula 100 and/or needle 102. The subject inserts the needle into the subject's skin by adhering the needle housing unit to the skin.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. An apparatus for administering a substance to a subject, the apparatus comprising:
   a housing including a housing base and a housing top, the housing base having a bottom surface, the bottom surface defining a base plane;
   an adhesive secured to the bottom surface of the housing base, the adhesive configured to secure the housing base to skin of the subject in a mounted configuration;
   a substantially cylindrical vial within the housing having a distal end, a proximal end and a longitudinal axis extending between the distal end and the proximal end, at least a portion of the substance located within the vial;
   a stopper slidably mounted within the vial, the stopper configured for movement along the longitudinal axis, the longitudinal axis being substantially parallel to the base plane;
   a first threaded element secured to the stopper;
   an activation mechanism within the housing, the activation mechanism including a movable button, a spring and a needle having a needle tip;

the needle being in communication with the vial and operatively connected to the button, the button movable between an initial position, wherein the needle tip is positioned within the housing and an extended position, wherein the needle tip extends out of the housing beyond the base plane, the button being biased toward the initial position by the spring;

a motor within the housing and a motor cog coupling the motor with the first threaded element, the motor being configured to rotate the first threaded element via the motor cog, to, in turn, distally advance the stopper to push at least a portion of the substance out of the vial and through the needle;

a battery within the housing to power the motor;

a control unit within the housing, the control unit being in communication with the motor and the activation mechanism, the control unit configured to signal the motor to operate when the button moves from the initial position to the extended position; and a sensor configured to detect a parameter and transmit a signal to the control unit responsive to the parameter to control the rotation of the motor.

2. The apparatus of claim 1, wherein the sensor is configured to detect a physiological parameter of the subject and the signal transmitted to the control unit relates to the detected physiological parameter.

3. The apparatus of claim 1, wherein the sensor is configured to be implanted in the subject's body.

4. The apparatus of claim 1, wherein the motor cog is a first cog rotatably secured to the housing, the apparatus further comprising:

a second cog secured to an end of the first threaded element;

a second threaded element positioned at least partially within the vial; and the second threaded element being in threaded engagement with the first threaded element, the second cog being in threaded engagement with the first cog, the first cog in threaded engagement with the motor the apparatus configured such that activation of the motor causes the first cog to rotate, the second cog to rotate, the first threaded element to rotate and the second threaded element and the stopper to translate along the longitudinal axis to administer at least a portion of the substance to the subject.

5. The apparatus of claim 1, wherein the sensor is comprised of a wireless sensor.

6. The apparatus of claim 1, further comprising:

a vial piercing mechanism within the housing, the vial having a seal at the distal end that is pierced by the vial piercing mechanism when the vial is inserted into the housing.

7. The apparatus of claim 6, further comprising:

a tube connected to the vial piercing mechanism, the tube configured to fluidly connect the vial piercing mechanism to the activation mechanism.

8. The apparatus of claim 1, further comprising:

a second threaded element threadingly engaged with the first threaded element and positioned on the longitudinal axis, the second threaded element and the first threaded element being at least partially positioned within the vial, the second threaded element and the first threaded element moving telescopically relative to each other when the motor is activated.

9. The apparatus of claim 1, further comprising:

a holding portion mounted to the housing and associated with the activation mechanism; and a structural element slidably mounted to the holding portion.

10. The apparatus of claim 9, wherein the structural element includes a protrusion, the protrusion assisting in maintaining the button in the initial position.

11. The apparatus of claim 1, wherein the needle is oriented substantially perpendicular to the base plane.

12. The apparatus of claim 1, wherein the vial includes a protrusion protruding from an inner surface and the first threaded element includes groove in an outer surface, the protrusion positioned in the groove to limit rotation of the first threaded element relative to the vial.

* * * * *